United States Patent
Viola

(10) Patent No.: US 8,292,147 B2
(45) Date of Patent: Oct. 23, 2012

(54) SURGICAL STAPLER HAVING AN ARTICULATION MECHANISM

(75) Inventor: Frank J. Viola, Sandy Hook, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/047,908

(22) Filed: Mar. 15, 2011

(65) Prior Publication Data
US 2011/0163149 A1   Jul. 7, 2011

Related U.S. Application Data

(62) Division of application No. 12/244,797, filed on Oct. 3, 2008, now Pat. No. 7,909,220.

(60) Provisional application No. 60/997,775, filed on Oct. 5, 2007.

(51) Int. Cl.
*A61B 17/068* (2006.01)

(52) U.S. Cl. .............. 227/175.1; 227/19; 227/176.1; 227/179.1; 227/180.1

(58) Field of Classification Search ............. 227/175.1, 227/19, 176.1, 179.1, 180.1; 74/63, 5 R, 74/640; 475/207, 164
See application file for complete search history.

(56) References Cited

U.S. PATENT DOCUMENTS

| | | | |
|---|---|---|---|
| 37,165 A * | 11/1862 | Nietsche | 475/163 |
| 2,881,645 A | 4/1959 | Kruchten | |
| 2,952,456 A | 9/1960 | Bunting | |
| 3,353,426 A * | 11/1967 | Wiser et al. | 475/163 |
| 3,551,987 A | 1/1971 | Wilkinson | |
| 4,343,200 A | 8/1982 | Alworth et al. | |
| 4,515,028 A | 5/1985 | VanDerlinden et al. | |
| 4,550,630 A * | 11/1985 | Remus | 475/163 |
| 4,821,393 A | 4/1989 | Spigarelli | |
| 4,946,428 A * | 8/1990 | Barozzi | 475/164 |
| 5,042,707 A | 8/1991 | Taheri | |
| 5,258,008 A | 11/1993 | Wilk | |
| 5,330,486 A | 7/1994 | Wilk | |
| 5,383,880 A | 1/1995 | Hooven | |
| 5,395,030 A | 3/1995 | Kuramoto et al. | |

(Continued)

FOREIGN PATENT DOCUMENTS

DE    4221403 A1    1/1994
(Continued)

OTHER PUBLICATIONS

European Search Report for EP 08253237.5-1265 date of completion is Jun. 15, 2009 (5 pages).

(Continued)

*Primary Examiner* — Lindsay Low
*Assistant Examiner* — Michelle Lopez

(57) ABSTRACT

An articulation mechanism for use with a surgical instrument includes a shaft, a first member disposed in mechanical cooperation with the articulation shaft, a second member disposed in mechanical cooperation with the shaft, and a flexible shaft having proximal and distal portions. The flexible member is operatively coupled to the first and second members. Upon rotation of the articulation shaft, at least one of the first and the second members moves longitudinally with respect to the other of the first and second members between a first position where the first and second members are approximated to each other and a second position where the first and second members are spaced apart from each other. This longitudinal motion causes the distal portion of the flexible member to articulate relative to the proximal portion.

11 Claims, 19 Drawing Sheets

U.S. PATENT DOCUMENTS

| | | | |
|---|---|---|---|
| 5,403,326 A | 4/1995 | Harrison et al. | |
| 5,433,721 A | 7/1995 | Hooven et al. | |
| 5,439,156 A | 8/1995 | Grant et al. | |
| 5,465,894 A | 11/1995 | Clark et al. | |
| 5,518,163 A | 5/1996 | Hooven | |
| 5,518,164 A | 5/1996 | Hooven | |
| 5,549,637 A | 8/1996 | Crainich | |
| 5,667,517 A | 9/1997 | Hooven | |
| 5,704,534 A | 1/1998 | Huitema et al. | |
| 5,704,865 A | 1/1998 | Rennerfelt | |
| 5,868,760 A | 2/1999 | McGuckin, Jr. | |
| 6,119,913 A | 9/2000 | Adams et al. | |
| 6,126,058 A | 10/2000 | Adams et al. | |
| 6,241,140 B1 | 6/2001 | Adams et al. | |
| 6,264,086 B1 | 7/2001 | McGuckin, Jr. | |
| 6,269,997 B1 | 8/2001 | Balazs et al. | |
| 6,302,311 B1 | 10/2001 | Adams et al. | |
| 6,358,259 B1 | 3/2002 | Swain et al. | |
| 6,398,795 B1 | 6/2002 | McAlister et al. | |
| 6,443,973 B1 | 9/2002 | Whitman | |
| 6,695,198 B2 | 2/2004 | Adams et al. | |
| 6,702,826 B2 | 3/2004 | Liddicoat et al. | |
| 6,716,233 B1 | 4/2004 | Whitman | |
| 6,821,282 B2 | 11/2004 | Perry et al. | |
| 7,025,732 B2 | 4/2006 | Thompson et al. | |
| 7,059,331 B2 | 6/2006 | Adams et al. | |
| 7,156,863 B2 | 1/2007 | Sonnenschein et al. | |
| 7,235,089 B1 | 6/2007 | McGuckin | |
| 7,331,584 B2 * | 2/2008 | Zhang et al. | 279/60 |
| 7,481,347 B2 * | 1/2009 | Roy | 227/175.1 |
| 7,575,144 B2 * | 8/2009 | Ortiz et al. | 227/175.1 |
| 7,708,182 B2 * | 5/2010 | Viola | 227/178.1 |
| 2001/0056282 A1 | 12/2001 | Sonnenschein et al. | |
| 2002/0049454 A1 | 4/2002 | Whitman et al. | |
| 2007/0114261 A1 | 5/2007 | Ortiz et al. | |
| 2007/0175961 A1 * | 8/2007 | Shelton et al. | 227/178.1 |
| 2007/0221701 A1 | 9/2007 | Ortiz et al. | |

FOREIGN PATENT DOCUMENTS

| | | |
|---|---|---|
| DE | 4300307 | 7/1994 |
| EP | 0634144 A | 1/1995 |
| EP | 2044891 A | 4/2009 |
| WO | WO 99/15090 | 4/1999 |
| WO | WO 00/67834 | 11/2000 |
| WO | WO 2008/101228 | 8/2008 |

OTHER PUBLICATIONS

Kedrowski et al. "Nutating Gear Drivetrain for a Cordless Screwdriver", Mechanical Engineering, ASME. New York, US, vol. 116, No. 1, Jan. 1, 1994, pp. 70-74.

European Search Report for EP 08253237.5-1265 date of completion is Jan. 9, 2009 (6 pages).

European Search Report for EP 08 25 3192 dated Jun. 10, 2010 (4 pages).

* cited by examiner

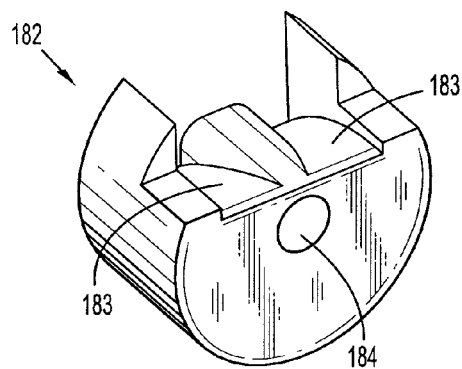
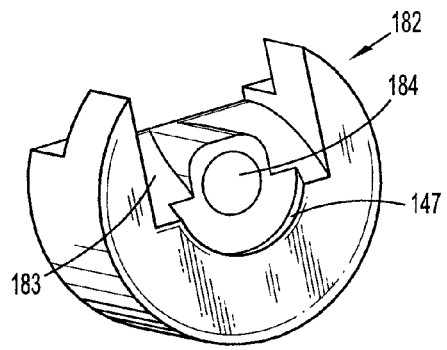
FIG. 6  FIG. 7
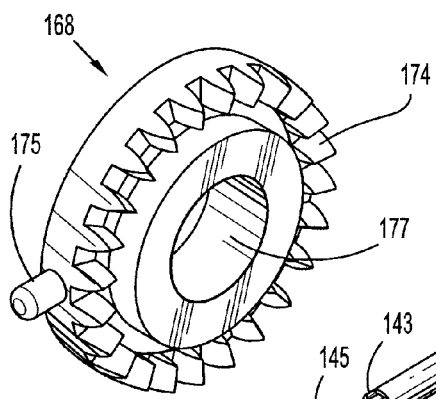
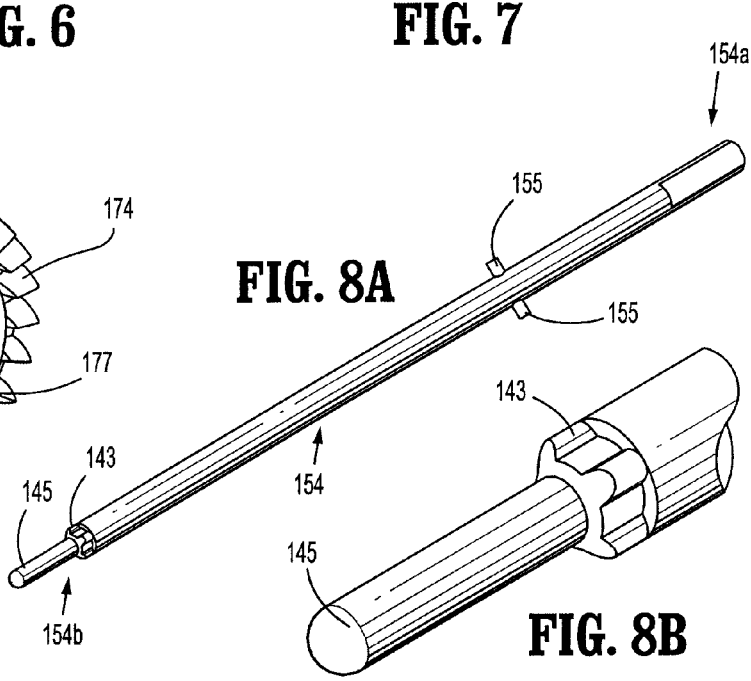
FIG. 8  FIG. 8A  FIG. 8B
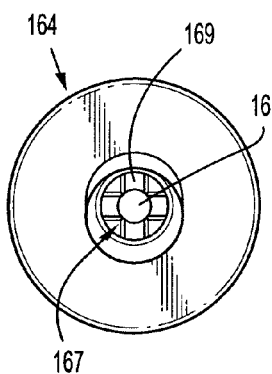
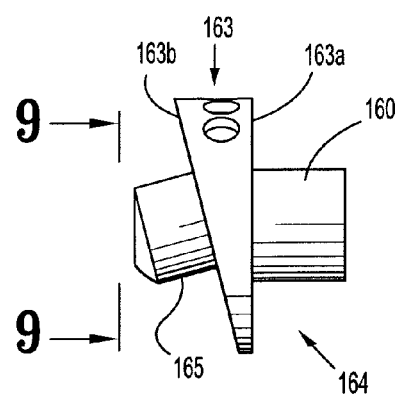
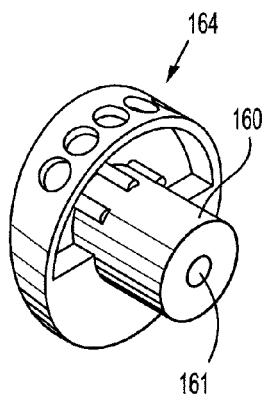
FIG. 9  FIG. 10  FIG. 11

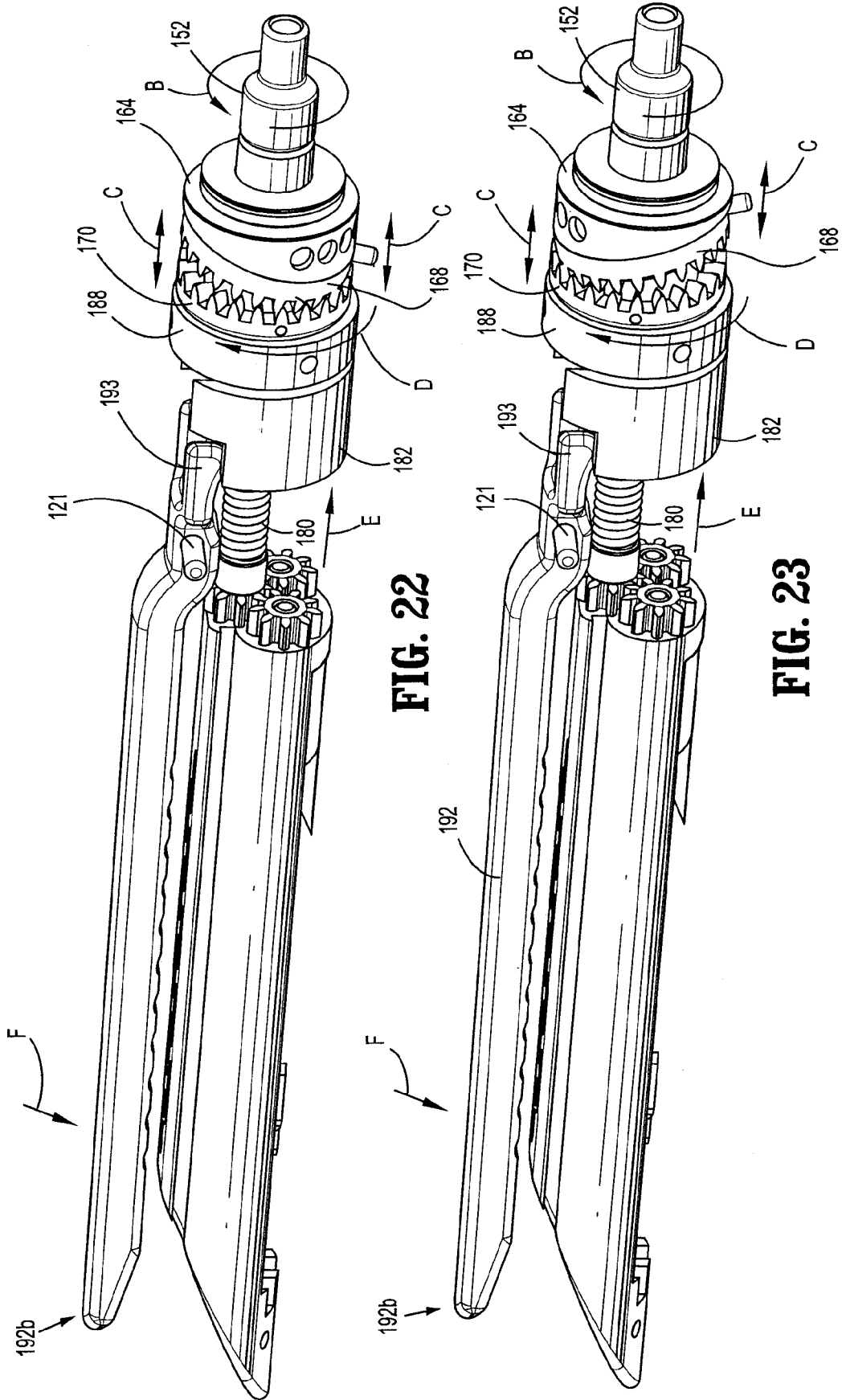

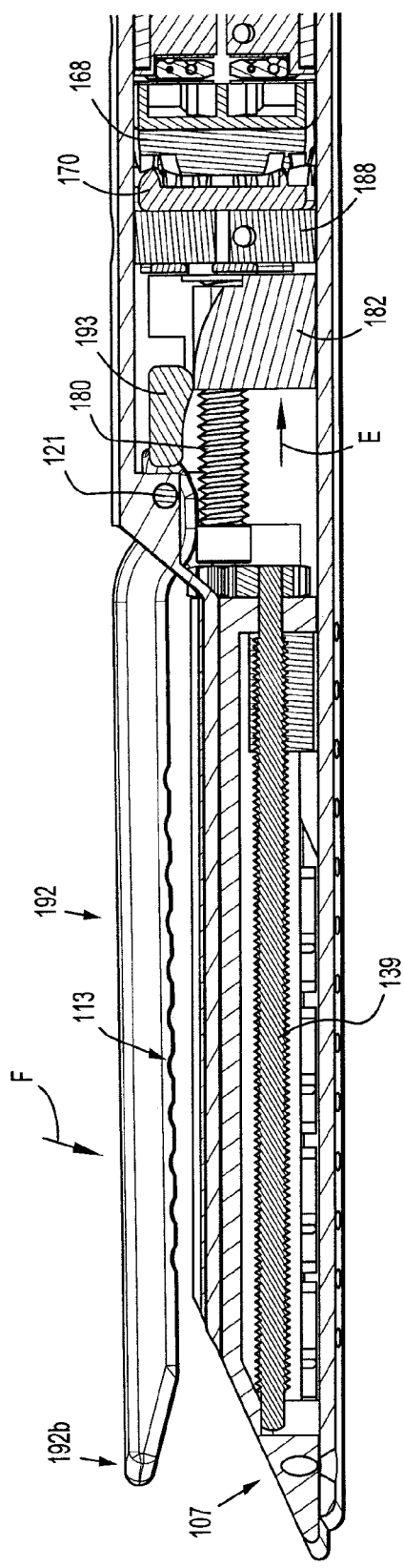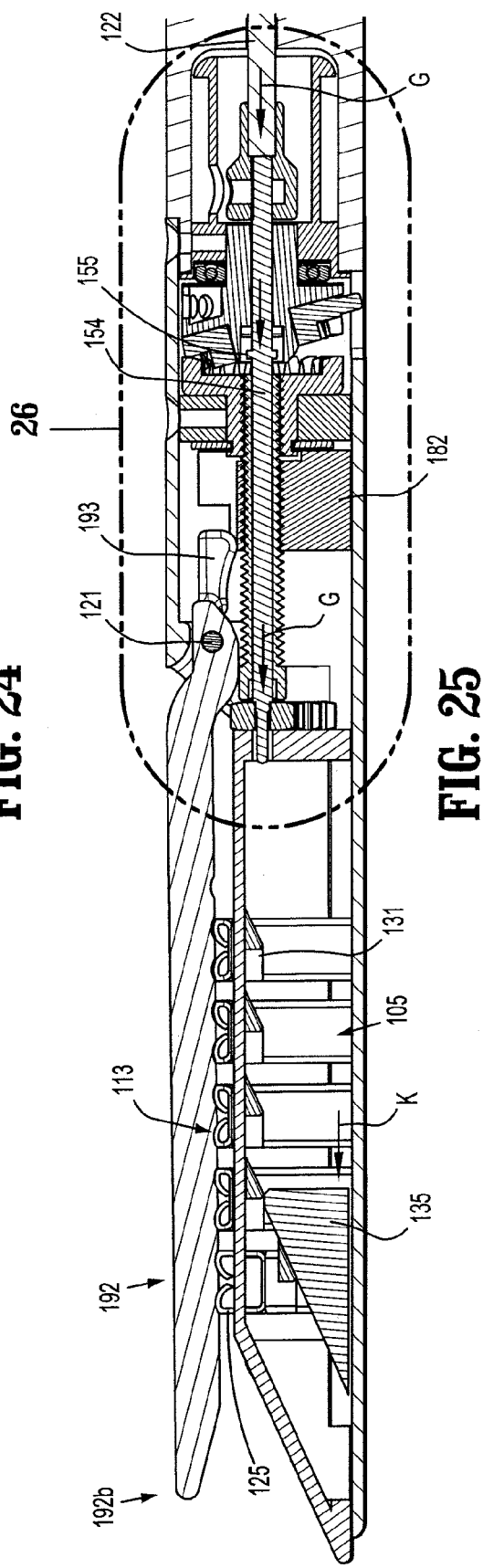

SURGICAL STAPLER HAVING AN ARTICULATION MECHANISM

CROSS-REFERENCE TO RELATED APPLICATIONS

This application is a divisional of U.S. application Ser. No. 12/244,797 filed Oct. 3, 2008, now U.S. Pat. No. 7,909,220 which claims benefit of application No. 60/997,775 filed Oct. 5, 2007, and the disclosures of each of the above-identified applications are hereby incorporated by reference in their entirety.

BACKGROUND

1. Technical Field

The present disclosure relates to apparatus and methods for surgical procedures. More particularly, the present disclosure relates to a surgical stapler and an articulation mechanism for use therewith.

2. Description of Related Art

Surgical instruments for fastening tissue are well known. Some surgical fastening devices first clamp tissue between opposing jaw structures and then join them with surgical fasteners. Several kinds of surgical instruments are specifically adapted for use in various procedures such as end-to-end anastomosis, endoscopic gastrointestinal anastomosis, transverse anastomosis, among others. U.S. Pat. Nos. 5,915,616; 6,202,914; 5,865,361; and 5,964,394 describe examples of surgical fastening instruments. Although these surgical fastening instruments typically employ surgical staples, other kinds of fasteners, such as two-part polymeric fasteners, may be used.

Surgical fastening instruments typically include two opposing jaw structures adapted to capture tissue. One jaw structure usually contains a staple cartridge housing a plurality of staples. The staples may be arranged in a single row or a plurality of rows. The other jaw structure has an anvil that defines a surface for forming the staple legs as the staples are driven from the staple cartridge. The surgical fastening instruments also include one or more cam members configured to effect the stapling operation. During use, the cam members act upon staple pushers and eject the staples either sequentially or simultaneously from the staple cartridge. The staple cartridge may include a knife adapted to cut or open the stapled tissue between the rows of staples. U.S. Pat. Nos. 3,079,606 and 3,490,675 disclose examples of this kind of instrument.

Certain surgical fastening instruments include articulating mechanisms to articulate a tool assembly or an end effector. An articulation mechanism may have an articulation actuator, a plurality of pulleys, and a plurality of articulation cables. The articulation actuator is operatively coupled to the articulation cables, and a portion of each articulation cable is disposed in a corresponding pulley. In operation, the articulation cables move longitudinally in proximal and distal directions upon actuation of the articulation actuator. As the articulation cables move longitudinally, the pulleys rotate and movement of the articulation cables causes articulation of the end effector. U.S. patent application Ser. No. 2007/0108252, which is assigned to U.S. Surgical, a division of Tyco Healthcare Group LP and is hereby incorporated by reference in its entirety, describes an example of this kind of articulation mechanism.

SUMMARY

The present disclosure relates to an articulation mechanism for use with a surgical instrument. This articulation mechanism includes a shaft, a first member disposed in mechanical cooperation with the articulation shaft, a second member disposed in mechanical cooperation with the shaft, and a flexible shaft having proximal and distal portions. The flexible member is operatively coupled to the first and second members. Upon rotation of the articulation shaft, at least one of the first and the second members moves longitudinally with respect to the other of the first and second members between a first position where the first and second members are approximated to each other and a second position where the first and second members are spaced apart from each other. This longitudinal motion causes the distal portion of the flexible member to articulate relative to the proximal portion.

The present disclosure also relates to a surgical fastening instrument including a flexible shaft and a nutating gear drive operatively connected to the flexible shaft. The nutating gear is configured to reduce the speed and increase the torque potential of the flexible shaft. The surgical fastening instrument further includes a drive shaft configured to be selectively attached to the nutating gear drive.

BRIEF DESCRIPTION OF THE DRAWINGS

Embodiments of the presently disclosed surgical stapler are described herein with reference to the accompanying drawings, wherein:

FIG. 6 is a front perspective view of a clamp cam;

FIG. 7 is a rear perspective view of the clamp cam of FIG. 6;

FIG. 8 is a perspective view of a crown stator;

FIG. 8A is a perspective view of a drive shaft;

FIG. 8B is an enlarged perspective view of a distal portion of the drive shaft of FIG. 8A;

FIG. 9 is a front view of a wobbler;

FIG. 10 is a side view of the wobbler of FIG. 9;

FIG. 11 is a rear perspective view of the wobbler of FIG. 9;

FIG. 22 is a perspective view of the nutating gear drive and the tool assembly of the surgical instrument of FIG. 1, showing a lower portion of the crown stator engaging a crown gear;

FIG. 23 is a perspective view of the nutating gear drive and the tool assembly of the surgical instrument of FIG. 1, showing an upper portion of the crown stator engaging the crown gear;

FIG. 24 is a side cross-sectional view of the tool assembly of the surgical instrument of FIG. 1, showing the a long lead screw, a clamp cam, and a nutating gear drive;

FIG. 25 is a side cross-sectional view of the tool assembly of the surgical instrument of FIG. 1, showing an actuation sled engaging pushers;

DETAILED DESCRIPTION OF THE EMBODIMENTS

Figure 1:
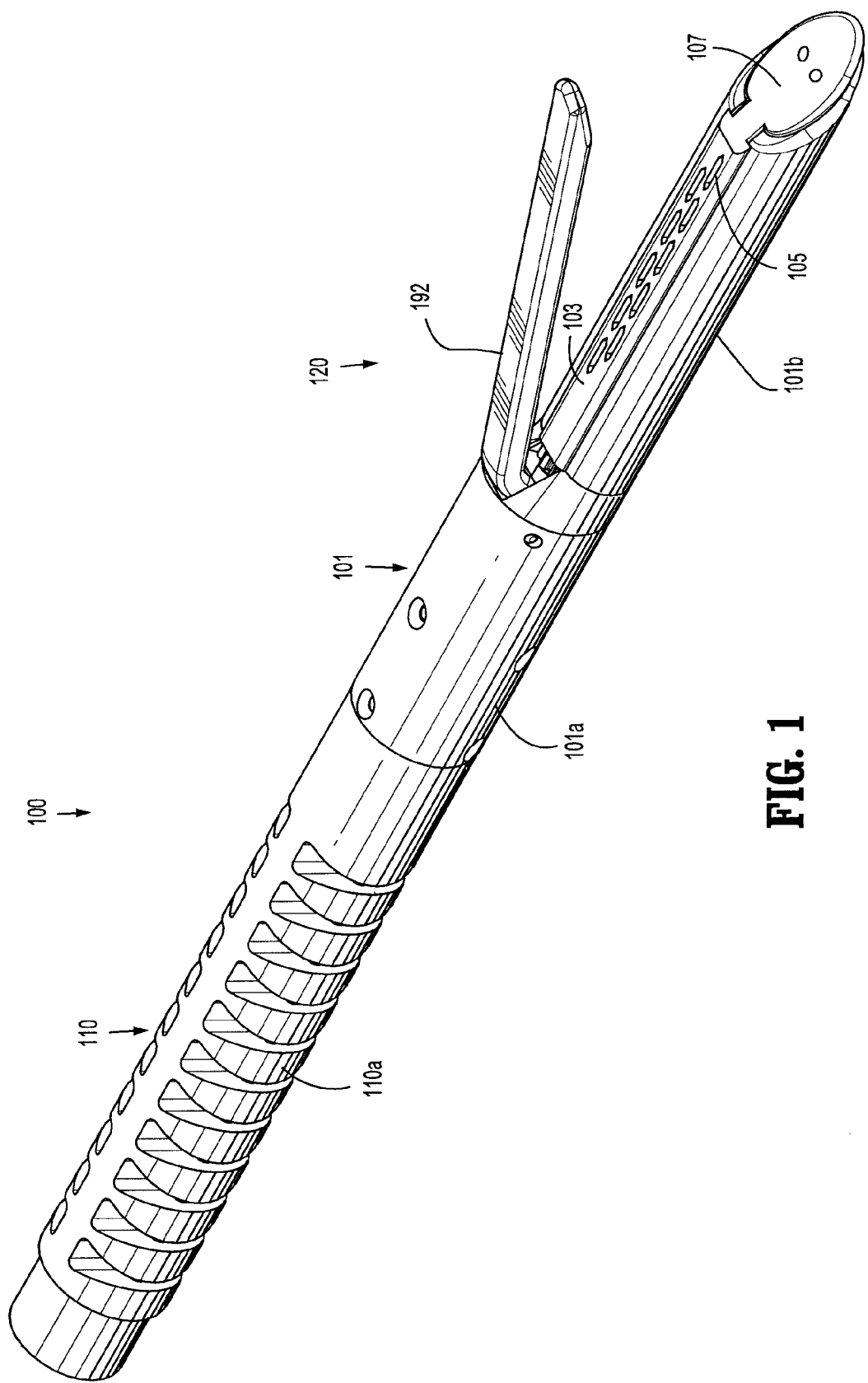
FIG. 1 is a perspective view of a surgical instrument according to an embodiment of the present disclosure.

Embodiments of the presently disclosed surgical instrument will now be described in detail with reference to the drawings wherein like reference numerals identify similar or identical elements. In the drawings and in the description that follows, the term "proximal," as is traditional, will refer to the end of the surgical instrument that is closest to the operator, while the term "distal" will refer to the end of the surgical instrument that is farthest from the operator.

Figure 2:
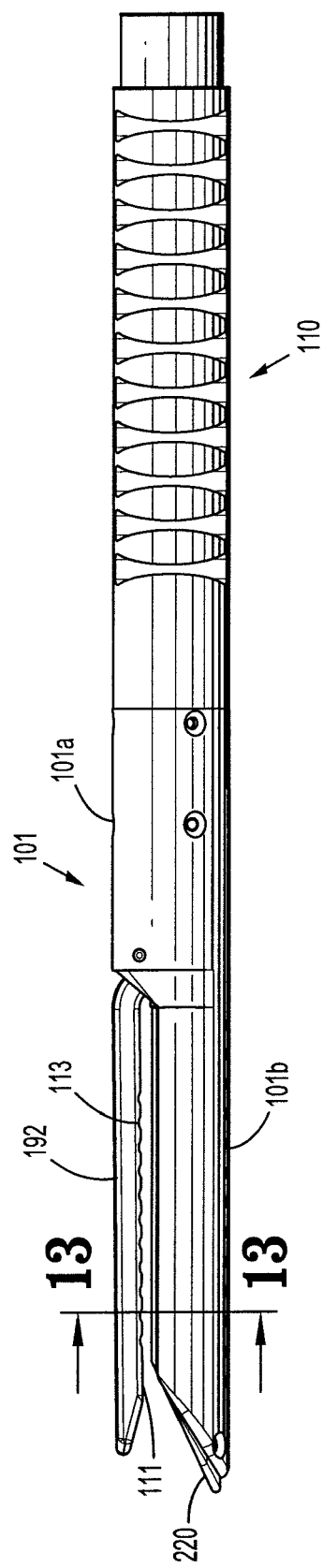
FIG. 2 is a side view of the surgical instrument of FIG. 1.
Figure 3:
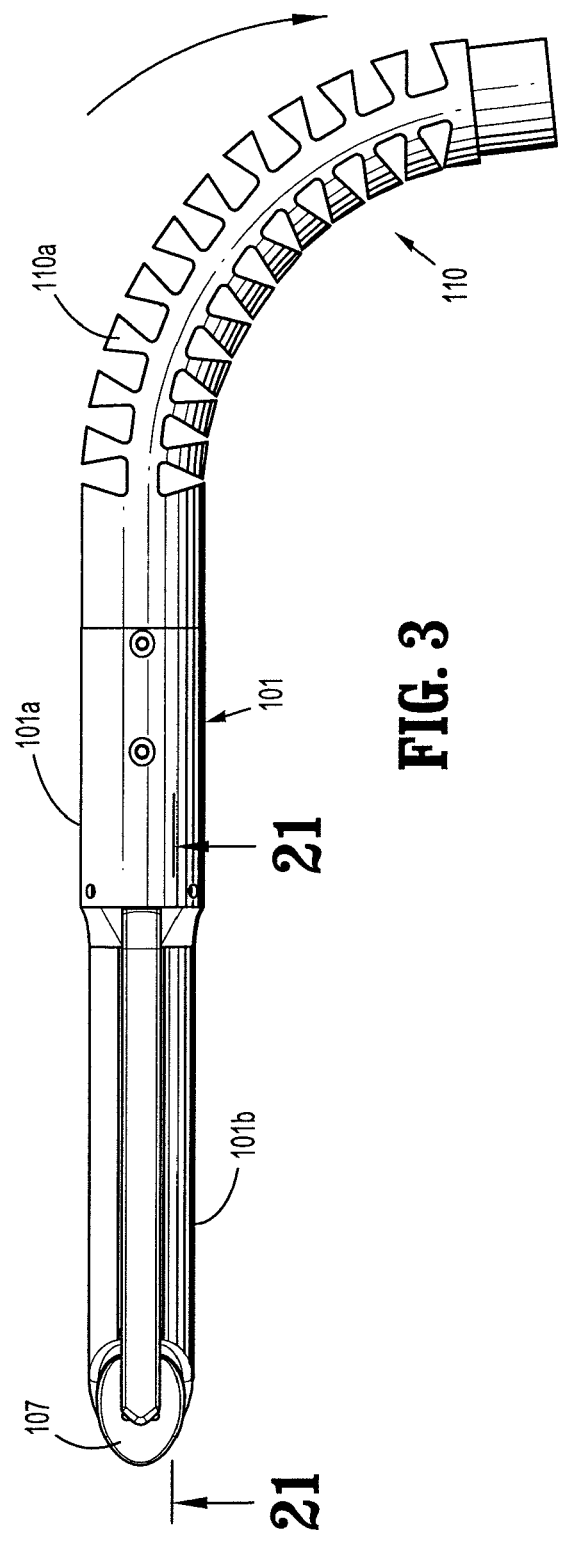
FIG. 3 is an top view of the surgical instrument of FIG. 1, showing articulation of a flexible member.

Referring to FIGS. 1-3, a surgical instrument is generally designated as 100. Surgical instrument 100 includes a flexible member 110 and a tool assembly 120. Flexible member 110 is at least partially formed from a plurality of generally wedge shaped sections 110a. Wedge shaped sections 110a are spaced apart from one another. When flexible member 110 is in a first state (FIG. 2), a first distance exists between wedge sections 110a. As flexible member 110 is repositioned from the first state toward a second state (FIG. 3), the distance between wedge sections 110a on at least one side of flexible member 110 increases. Wedge sections 110a have a wedge shape, but other shapes are also contemplated.

Tool assembly 120 is operatively coupled to flexible member 110 and includes a support member 101, a cartridge 107, and an anvil 192. Support member 101 has a proximal body portion 101a and a distal body portion 101b. Proximal body portion 101b is connected to a distal end of flexible member 110. Distal body portion 101b supports cartridge 107. It is contemplated that cartridge 107 may be a replaceable cartridge. Anvil 192 is configured to pivot relative to cartridge 107. In addition, anvil 192 has a tissue contacting surface 111 having a plurality of fastener deforming concavities 113. During operation, fastener deforming concavities 113 deform the legs of fasteners driven toward anvil 192 (see FIG. 25). Cartridge 107 also has a tissue contacting surface 103 and retention slots 105 adapted to receive fasteners. Retention slots 105 may be arranged in longitudinal rows. In the depicted embodiment, cartridge 107 includes two longitudinal rows of retention slots 105 although other arrangements of retention slots 105 are within the scope of this disclosure. In operation, fasteners exit through retention slots 105 upon actuation of tool assembly 120.

Figure 4:
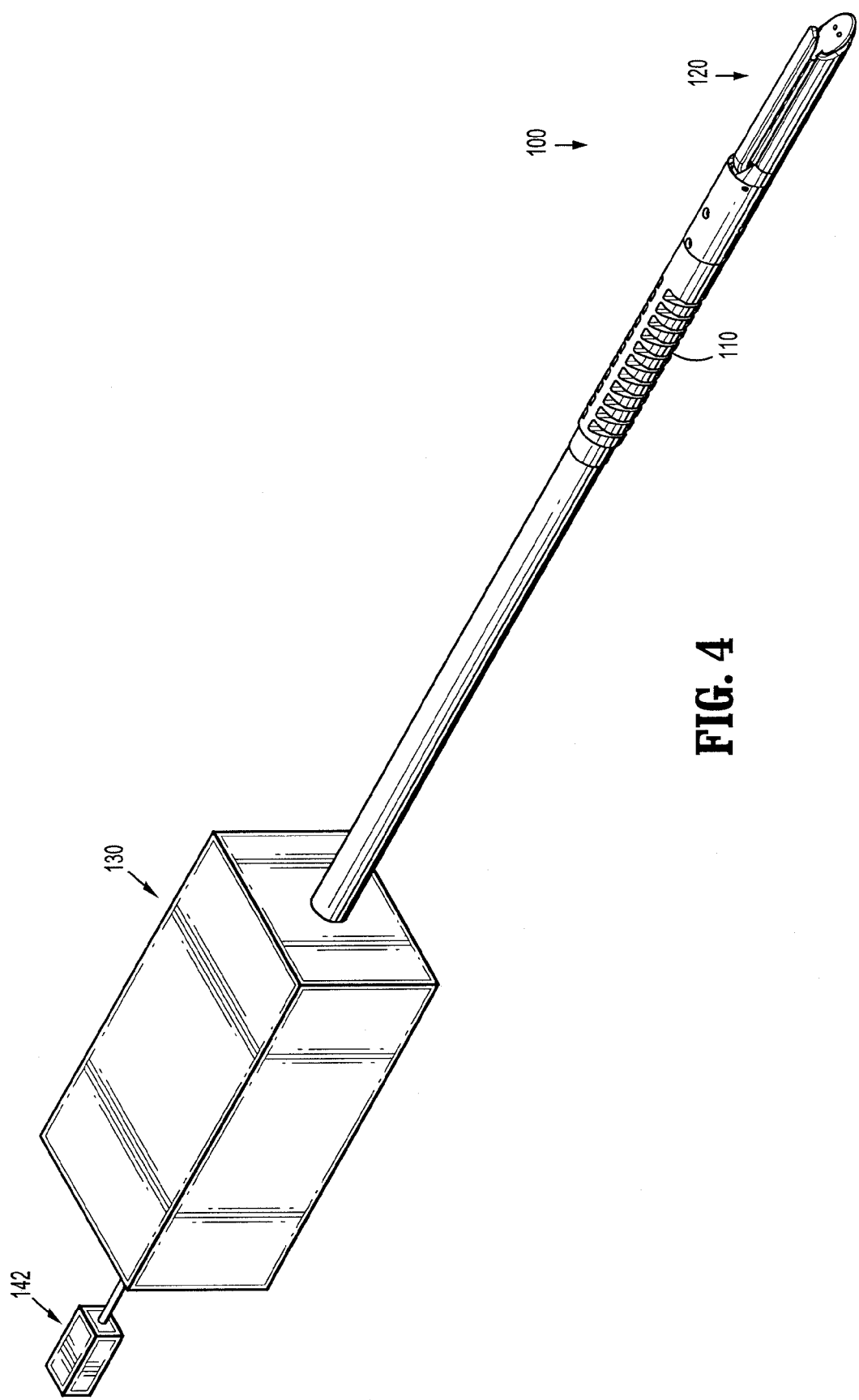
FIG. 4 is a perspective view of the surgical instrument of FIG. 1 connected to an actuation apparatus and a motor assembly.
Figure 19:
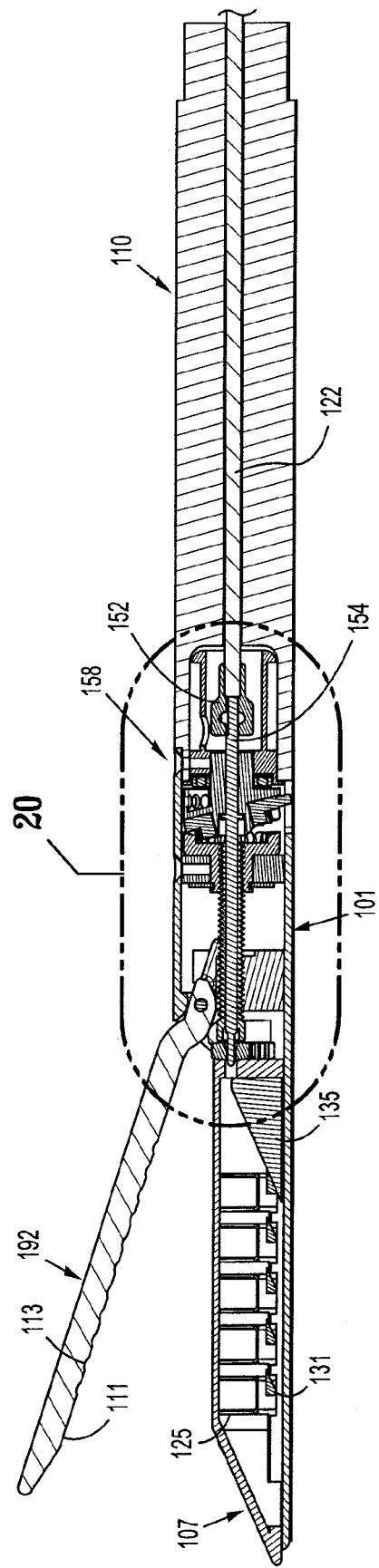
FIG. 19 is a side cross-sectional view of the surgical instrument of FIG. 1.

With reference to FIG. 4, surgical instrument 100 is operatively coupled to an actuation apparatus 130 for actuating tool assembly 120. The present disclosure contemplates that any suitable actuation apparatus may be employed to actuate tool assembly 120. In particular, actuation apparatus 130 is operatively coupled to flexible member 110. A motor assembly 142 is mechanically coupled to actuation apparatus 130. Although the drawings show motor assembly 142 positioned outside actuation apparatus 130, one skilled in the art will recognize that motor assembly 142 may be located within actuation apparatus 130. Motor assembly 142 may be powered by an electric motor or a pneumatic motor. Alternatively, actuation apparatus 130 may be powered by other kinds of driving devices including manual actuators. Irrespective of the driving devices utilized, actuation apparatus 130 is capable of rotating a flexible shaft 122 (see FIG. 19) partially disposed within flexible member 110.

With reference to FIGS. 5 and 18-20, flexible member 110 partially retains a transition member 124 at its distal end 110b. Transition member 124 operatively connects flexible member 110 to nutating gear drive 158 and includes a cavity region 150. Cavity region 150 surrounds a coupling 152 adapted for connecting flexible shaft 122 to drive shaft 154. Drive shaft 154 includes at least one outwardly extending protrusion 155 for engaging a wobbler 164 of nutating gear drive 158 (see FIG. 20).

Figure 16:
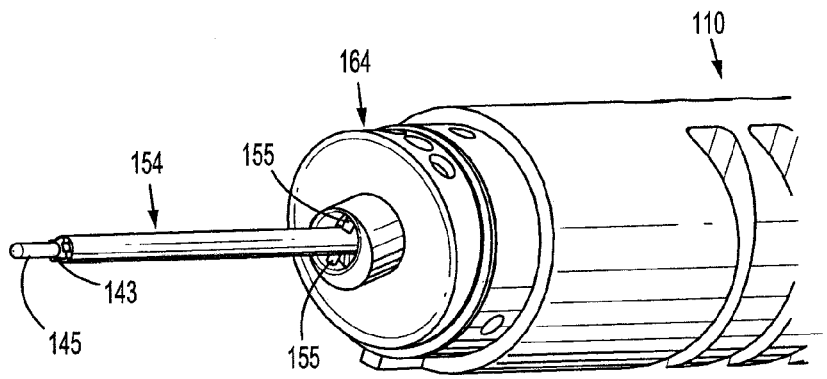
FIG. 16 is a perspective view of the distal end of the flexible member of FIG. 14 showing a wobbler and the drive shaft.
Figure 17:
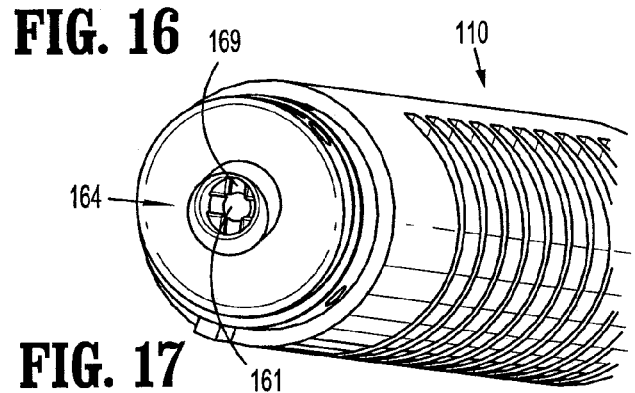
FIG. 17 is a perspective view of the distal end of the flexible member with the drive shaft removed.

Referring now to FIGS. 9-11, wobbler 164 of nutating gear drive 158 includes a tubular portion 160 having lumen 161 extending therethrough. Lumen 161 of tubular body 160 is adapted to receive drive shaft 154 (see FIG. 20). A pressing portion 163 surrounds tubular body 160 and has a proximal surface 163a and a distal surface 163b. Proximal surface 163a is substantially orthogonal to tubular portion 160. In contrast, distal surface 163b defines an angle with respect to tubular portion 160. Additionally, wobbler 164 includes an angled elongate portion 165 extending distally from distal surface 163b. Angled elongate portion 165 defines an angle with respect to tubular portion 162 and includes a hollow space 167 (see FIG. 20). Hollow space 167 encompasses a portion of drive shaft 154 and outwardly extending protrusions 155 (see FIG. 16). Angled elongate portion 165 also includes an engagement portion 169 adapted to engage the outwardly extending protrusions 155 of drive shaft 154 (see FIG. 17). During operation, outwardly extending protrusions 155 engage engagement portion 169 when drive shaft 154 is moved proximally. Once outwardly extending protrusions 155 engage engagement portion 169, drive shaft 154 drives wobbler 164. In the depicted embodiment, engagement portion 169 is a cross-shaped recess positioned on a proximal segment of angled elongate portion 165. Nonetheless, one skilled in the art will envision that engagement portion 169 may have any suitable configuration so long as it is able to engage outwardly extending protrusions 155.

Figure 20:
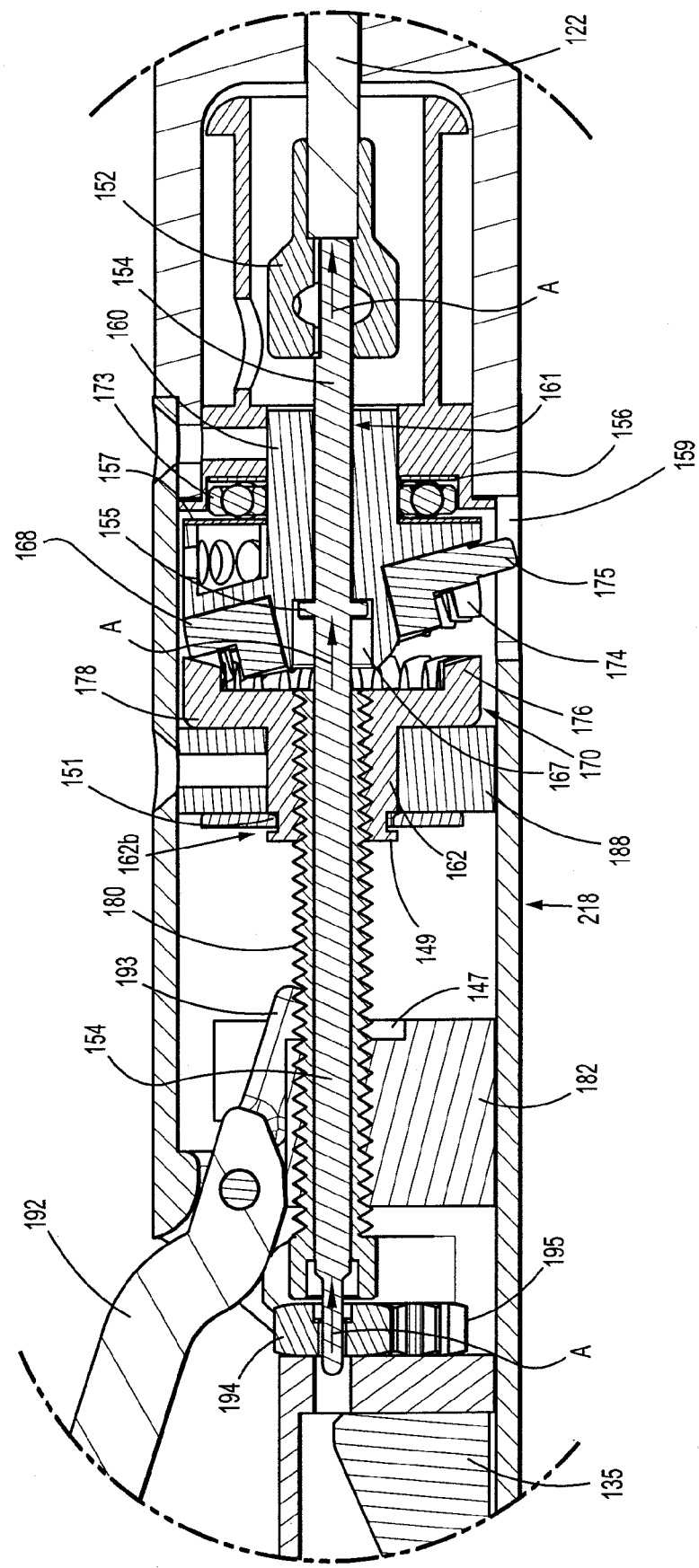
FIG. 20 is a side cross-sectional view of the transition member, the nutating gear drive, and the clamp cam taken around section 20 of FIG. 19.

Referring again to FIGS. 5 and 18-20, a first washer 156 surrounds tubular portion 160 of wobbler 164 and separates an internal surface 171 of transition member 124 from a bearing 173. Bearing 173 also surrounds tubular portion 160 of wobbler 164 and separates first washer 156 from a second washer 157. As seen in FIG. 20, first washer 156 is disposed within transition member 124. Bearing 173 is at least partially positioned within transition member 124. Second washer 157, however, is juxtaposed to proximal surface 163a of pressing portion 163. Distal surface 163b of pressing portion 163, in contrast, is disposed in juxtaposed alignment with a crown stator 168.

With reference to FIGS. 8 and 20, crown stator 168 includes a number of teeth 174, an opening 177, and a pin 175 extending outwardly. Teeth 174 face teeth 176 of a crown gear 170, as seen in FIG. 20. In operation, teeth 174 of crown stator 168 mesh with teeth 176 of crown gear 170. Opening 177 of crown stator 168 is adapted to receive angled elongate portion 165 of wobbler 164 (see FIG. 10). Pin 175 of crown stator 168 is slidably positioned in a slot 159 of support member 101. Slot 159 is located in a lower portion of proximal body portion 101a of support member 101. During operation, pin 175 inhibits the rotation of crown stator 168 while allowing crown stator 168 to wobble. The wobbling motion of crown stator 168 causes the rotation of crown gear 170.

Figure 18:
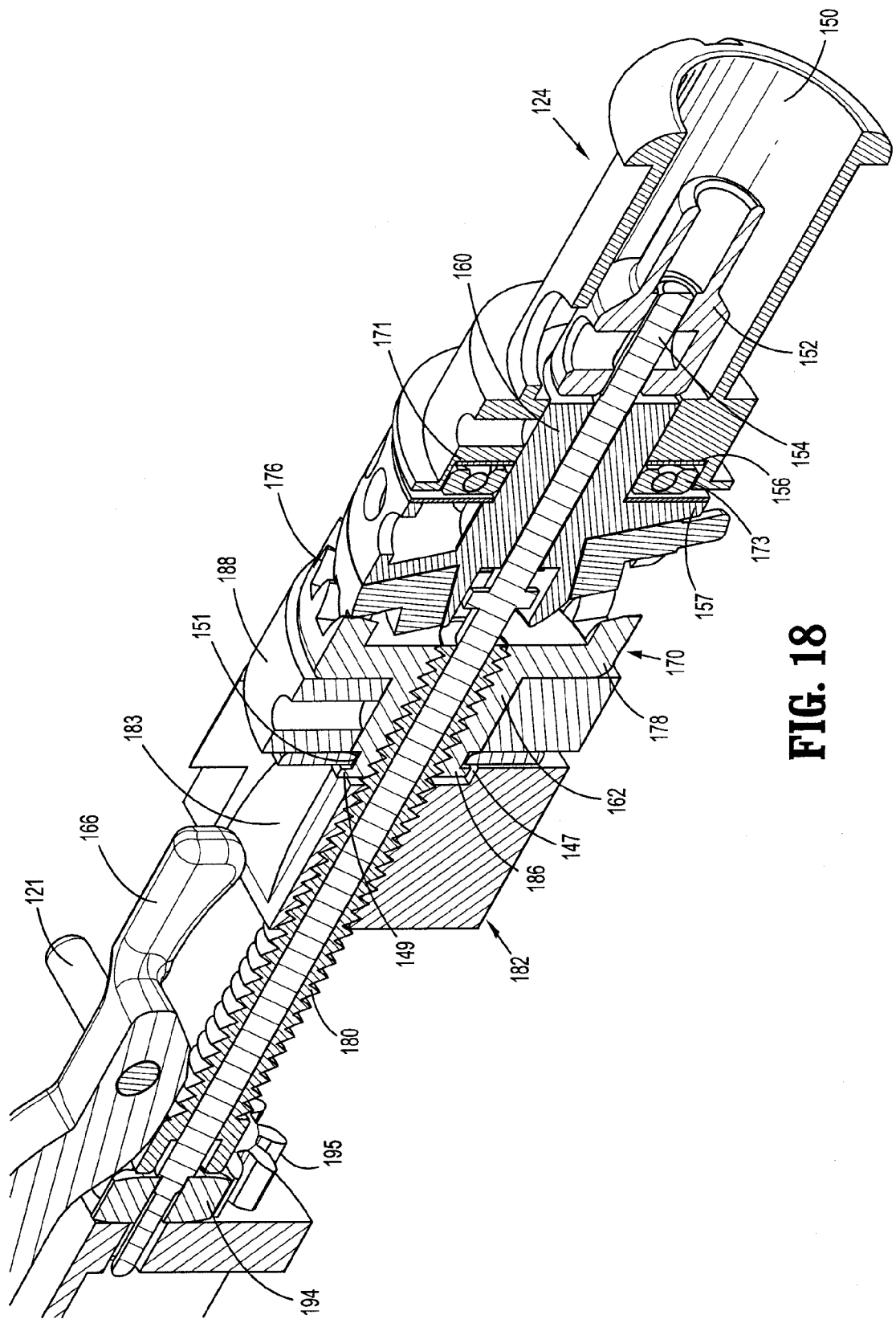
FIG. 18 is a perspective cross-sectional view of the transition member, the nutating gear drive, and the clamp cam of the surgical instrument of FIG. 1.

Referring again to FIGS. 5 and 18-20, crown gear 170 includes a plate 178, an elongate body 162, and bore 153 extending therethrough. A number of teeth 176 protrude proximally from plate 178. Bore 153 extends from plate 178 to elongate body 162 and is configured to receive a short lead screw 180. A proximal portion of short lead screw 180 is tightly locked to crown gear 170. In operation, short lead screw 180 rotates in response to a rotation of crown gear 170. A gear cage 188 surrounds elongate body 162 of crown gear 170 and is fixed to support member 101. In one embodiment, a screw secures gear cage 188 to support member 101. Gear cage 188 stabilizes crown gear 170 and is positioned adjacent to an E-ring 186. E-ring 186 is disposed in a recess 151 surrounding a distal end 162b of elongate body 162. Distal end 162b of elongate body 162 also includes a flange 149 to secure E-ring 186. Flange 149 sits on a recess 147 of clamp cam 182 when clamp cam 182 is positioned next to crown gear 170, as depicted in FIG. 18.

Figure 5:
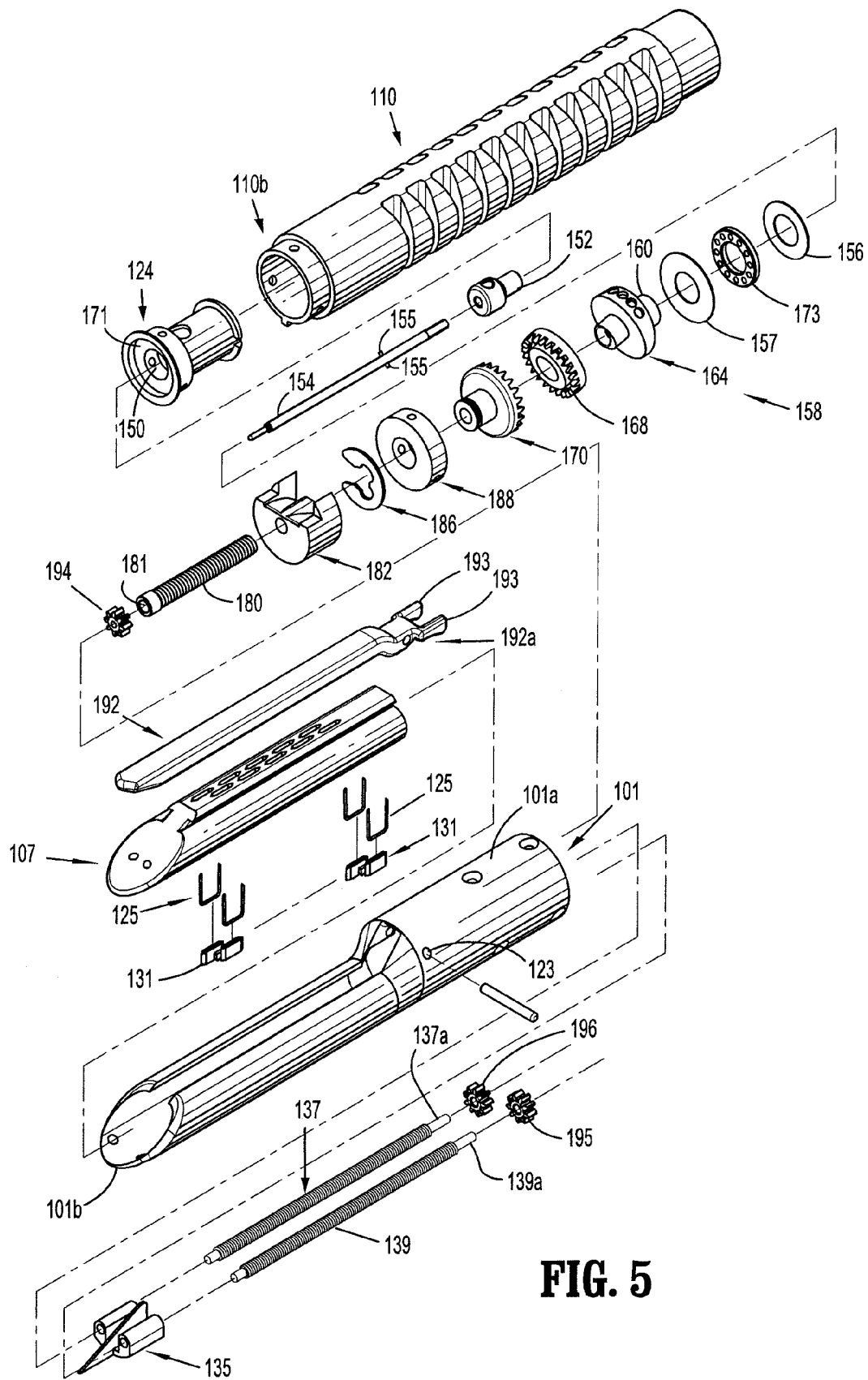
FIG. 5 is a perspective exploded view of the surgical instrument of FIG. 1.

With reference to FIGS. 5-7, clamp cam 182 includes a threaded bore 184 adapted to receive short lead screw 180 and at least one contoured surface 183 configured to receive at least one leg 193 disposed at a proximal portion 192a of anvil 192. Contoured surfaces 183 have a downward inclination in the proximal direction. During operation, a clockwise rotation of short lead screw 180 moves clamp cam 182 proximally through proximal body portion 101a of support member 101. When clamp cam 182 translates proximally, countered surfaces 193 urge legs 193 of anvil 192 in an upward direction. As legs 193 move upwardly, a distal portion 192b of anvil 192 moves toward cartridge 107 to clamp tissue.

With reference to FIGS. 5, 8A, 8B, 14, 15 and 20, short lead screw 180 includes a central lumen 181 adapted to receive a portion of drive shaft 154. A proximal portion 154a of drive shaft 154 is operatively connected to coupling 152, and a distal portion 154b is configured to be attached to a first pinion gear 194. In an embodiment, distal portion 154b has a tip 145 and a spline 143. First pinion gear 194 has a plurality of indentations 141 adapted to receive spline 143. When drive shaft 154 is moved distally, spline 143 engages indentations 141 of first pinion gear 194.

Figures 12, 13:
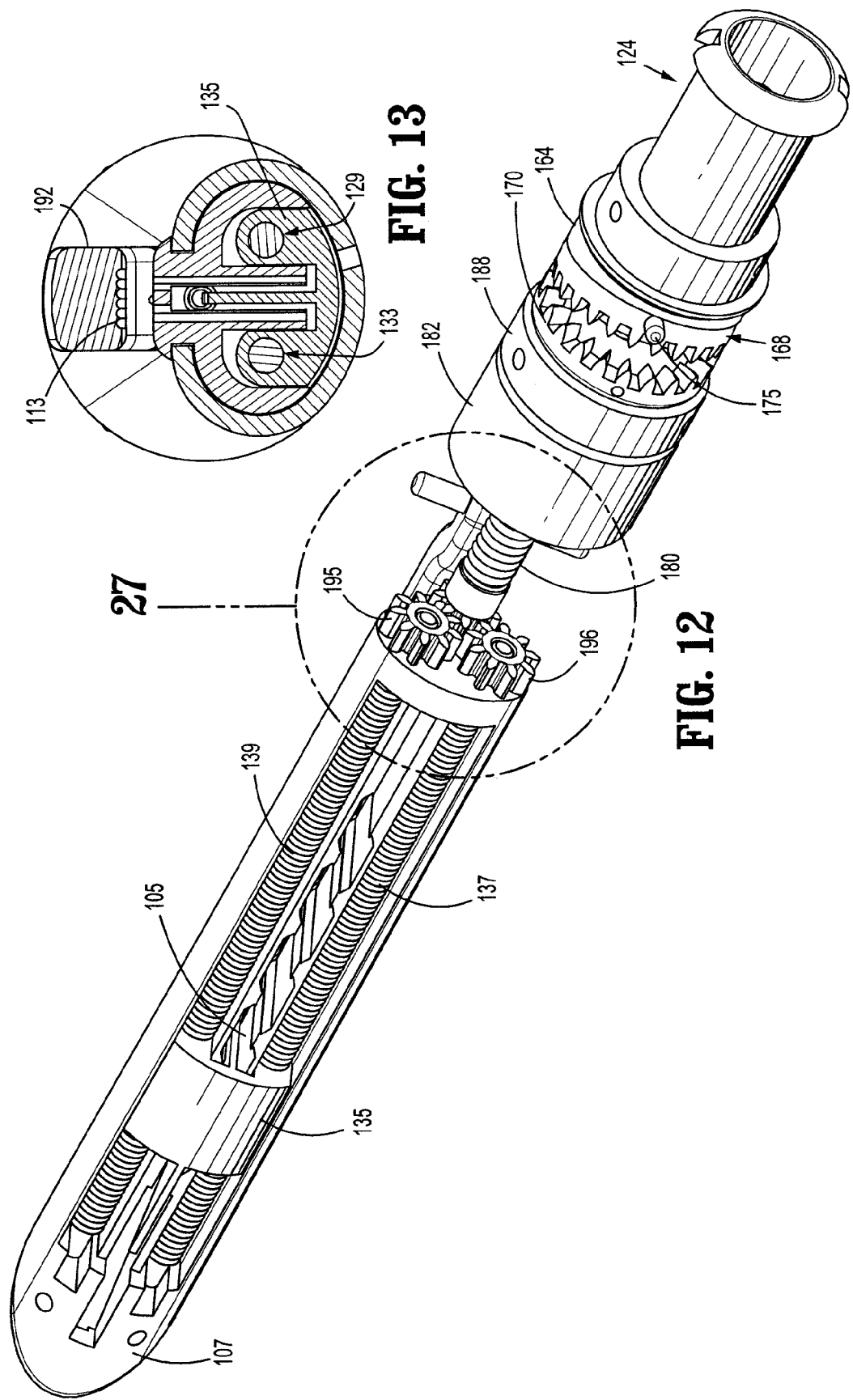
FIG. 12 is a bottom perspective view of a transition member, a nutating gear drive, and a tool assembly of the surgical instrument of FIG. 1.
FIG. 13 is a front cross-sectional view of the tool assembly taken along section line 13-13 of FIG. 2.
Figure 14:
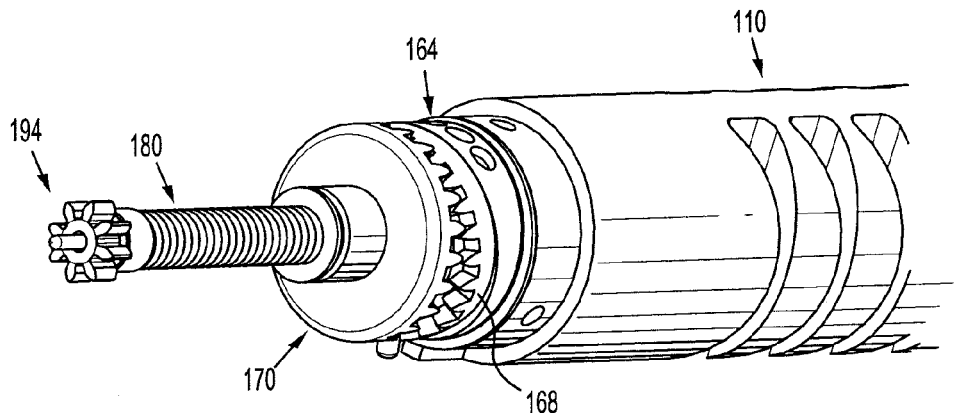
FIG. 14 is perspective view of the distal end of the flexible member of the surgical instrument of FIG. 1 illustrating a nutating gear drive.
Figure 15:
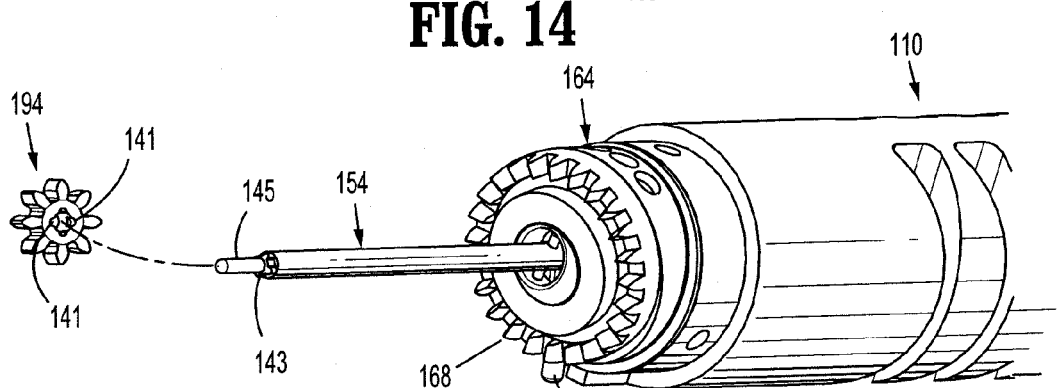
FIG. 15 is a perspective view of the distal end of the flexible member of FIG. 14 showing a pinion gear separated from a drive shaft.

With reference to FIGS. 5, 12, 13, and 18-20, first pinion gear 194 meshes simultaneously with second pinion gear 195 and third pinion gear 196 when drive shaft 154 is moved distally. Therefore, first pinion gear 194 is configured to mesh with second and third pinion gears 195, 196. Second pinion gear 195 is operatively attached to a proximal end 139a of first long lead screw 139, and third pinion gear 196 is operatively secured to a proximal end 137a of a second long lead screw 137. During operation, the rotation of second and third pinion gears 195, 196 causes the respective rotation of first and second long lead screws 139, 137. First and second long lead screws 139, 137 extend through cartridge 107 and are configured to engage an actuation sled 135. As seen in FIG. 13, actuation sled 135 includes two threaded holes 129, 133 for receiving respective first and second long lead screws 139, 137. In use, the counterclockwise rotation of first and second long lead screws 139, 137 advances actuation sled 135 through cartridge 107.

As discussed above, cartridge 107 includes a plurality of retention slots 105. Each retention slot 105 holds a pusher 131 and a fastener 125. In operation, actuation sled 135 acts upon pushers 131 to eject the fasteners 125 housed in retention slots 105. As fasteners 125 are driven toward anvil 192, fastener deforming concavities 113 deform the legs of fasteners 125.

Figure 21:
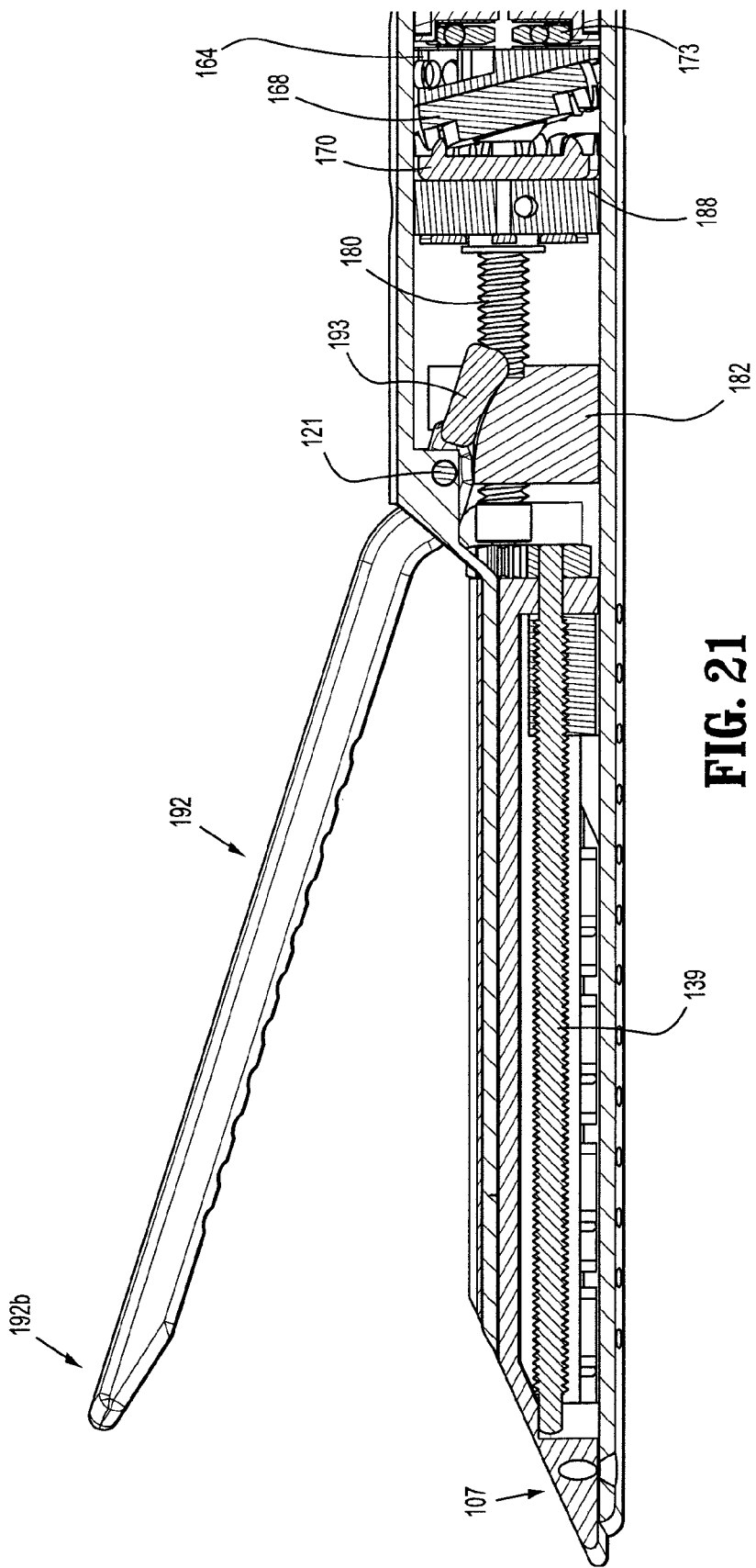
FIG. 21 is a side cross-sectional view of the tool assembly, the clamp cam, and the nutating gear drive taken along section line 21-21 of FIG. 3.

Proximal portion 192a of anvil 192 is pivotably connected to the proximal body portion 101a of support member 101. In one embodiment, proximal body portion 101a has a hole 123 configured to receive a pivot pin 121. Pivot pin 121 pivotably couples support member 101 and anvil 192. Consequently, anvil 192 moves from an open position to a clamped position upon actuation of actuation apparatus 130. In the open position, anvil 192 is spaced apart from cartridge 107, as seen in FIG. 21. In the clamped position, anvil 192 is disposed in juxtaposed alignment with cartridge 107, as shown in FIG. 24.

Surgical instrument 100 is capable of fastening body tissue. Referring now to FIGS. 20-27, the user places tool assembly 120 in the target surgical site. To this end, flexible member 110 may be articulated manually or by employing an articulation mechanism. (See FIG. 3).

After properly positioning tool assembly 120 in the desired surgical site, the user turns on motor assembly 142 to activate actuation apparatus 130. (See FIG. 4). Utilizing actuation apparatus 130, the user moves flexible shaft 122 proximally in the direction indicated by arrows "A." (See FIG. 20). Since flexible shaft 122 is connected to drive shaft 154, the proximal translation of flexible shaft 122 moves drive shaft 154 proximally. When drive shaft 154 is translated proximally, outwardly extending protrusions 155 engage in engagement portion 169 of wobbler 164, as illustrated in FIG. 20. Once outwardly extending protrusions 155 are engaged to engagement portion 169, the user rotates flexible shaft 122 to move anvil 192.

Motor assembly 142 drives actuation apparatus 130. Actuation apparatus 130 rotates flexible shaft 122 at high speed with a corresponding low torque value. The rotary motion of flexible shaft 122 causes the rotation of coupling 152 and drive shaft 154. The direction of the rotation of flexible shaft 122 ultimately determines the movement of anvil 192. If an anvil 192 is in an open position, as shown in FIG. 21, the user moves anvil 192 to a clamped position by rotating flexible shaft 122 in a counterclockwise direction, as indicated by arrows "B." (See FIGS. 22 and 23). The high speed, low torque rotation of flexible shaft 122 causes the rotation of drive shaft 154 and wobbler 164. The rotary motion of wobbler 164, in turn, causes crown stator 168 to wobble back and forth in the direction indicated by arrows "C." (See FIGS. 22 and 23). As crown stator 168 wobbles, only some teeth 174 of crown stator 168 mesh with teeth 176 of crown gear 170. The difference in the number of teeth between crown stator 168 and crown gear 170 dictates the speed reduction ratio of nutating gear drive 158. Specifically, when wobbler 164 effects one full rotation, crown gear 168 rotates an amount that is directly proportional to the difference in the number of teeth between crown stator 168 and crown gear 170.

In general, while crown stator 168 wobbles, crown gear 170 rotates clockwise at low speed, with a corresponding high torque potential, as indicated by arrows "D. (See FIGS. 22 and 23). The low speed rotation and high torque potential of crown gear 170 causes the rotation of short lead screw 180. Given that short lead screw 180 is threadably coupled to clamp cam 182, the clockwise rotation of short lead screw 180 moves clamp cam 182 proximally, as indicated by arrows "E." (See FIGS. 22-24). As clamp cam 182 moves proximally, legs 193 of anvil 192 move upwardly along contoured surfaces 183. When legs 193 move in an upward direction, anvil 192 pivots about pivot pin 121, thereby causing the distal portion 192b of anvil 192 to descend and clamp tissue, as indicated by arrows "F." (See FIGS. 22-24).

Figure 26:
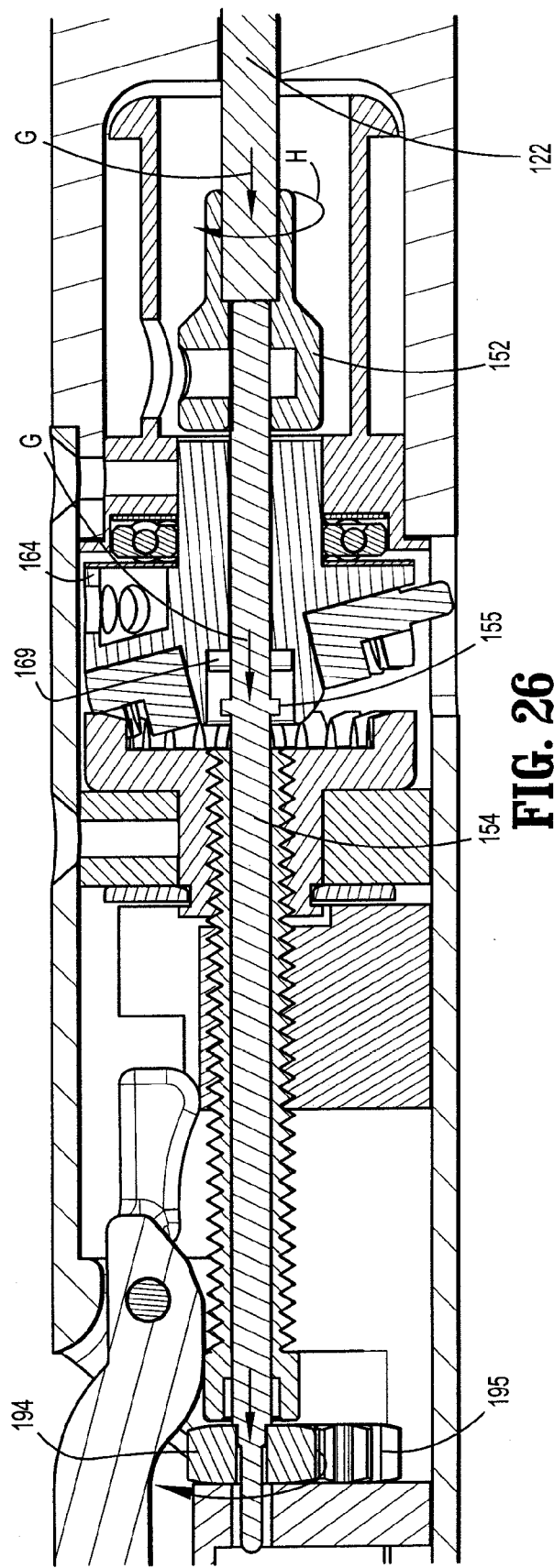
FIG. 26 is a cross-sectional side view the nutating gear drive and the transition member taken around section 26 of FIG. 25.
Figure 27:
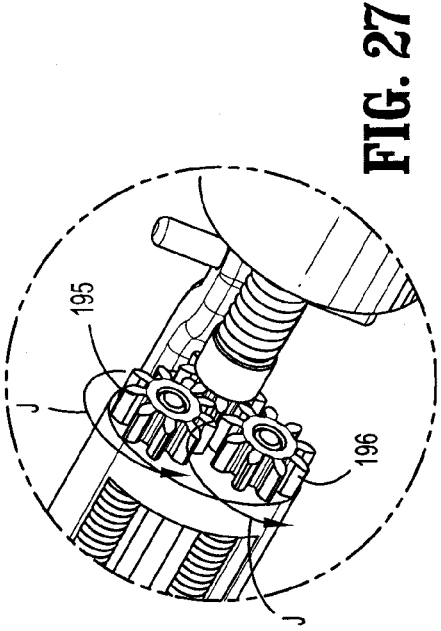
FIG. 27 is a perspective view of a second and third pinion gears taken around section 27 of FIG. 12.
Figure 28:
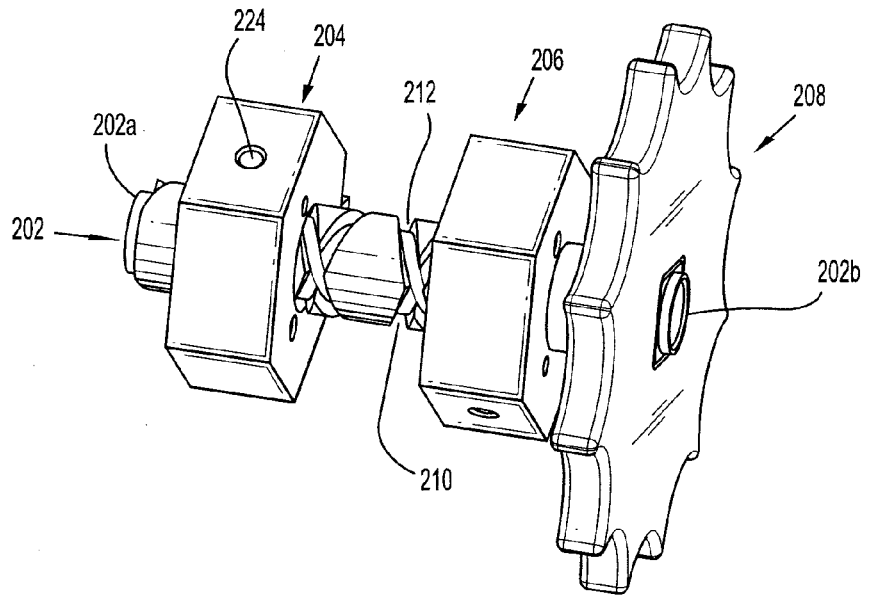
FIG. 28 is a side perspective view of an articulation mechanism according to an embodiment of the present disclosure.
Figure 29:
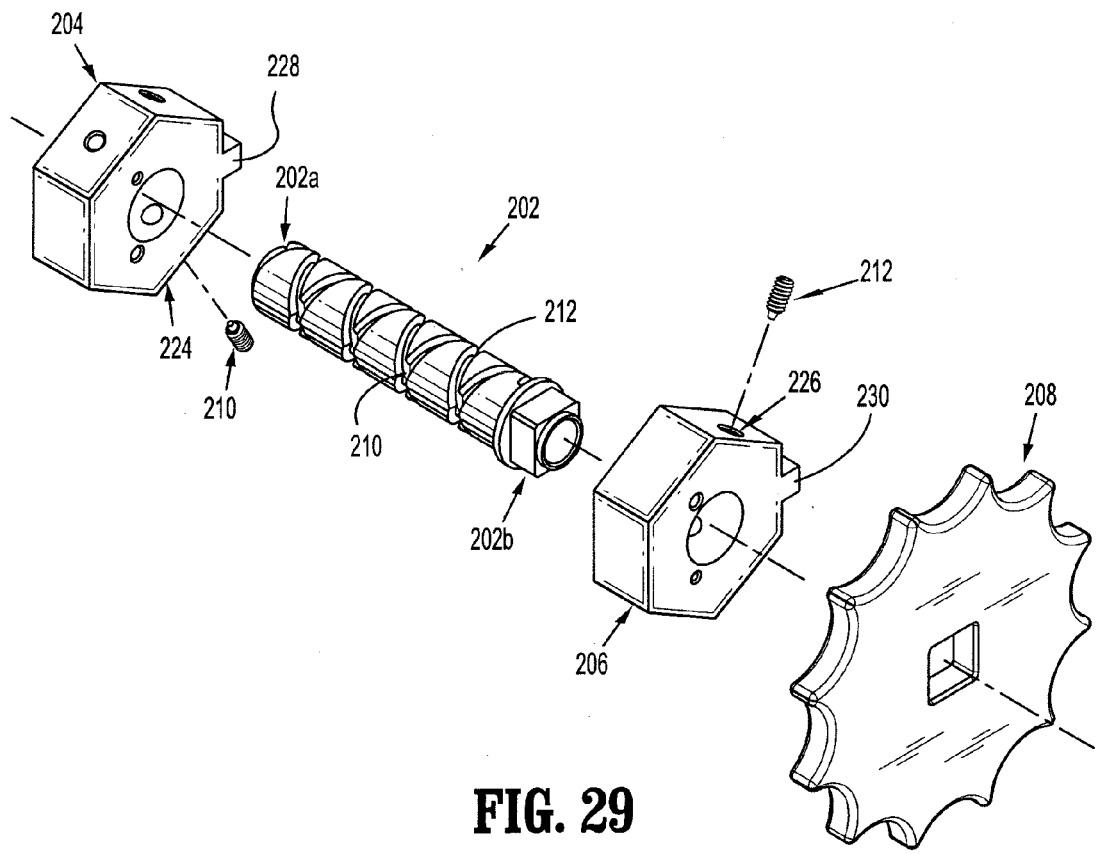
FIG. 29 is a exploded perspective view of the articulation mechanism of FIG. 28.
Figure 30:
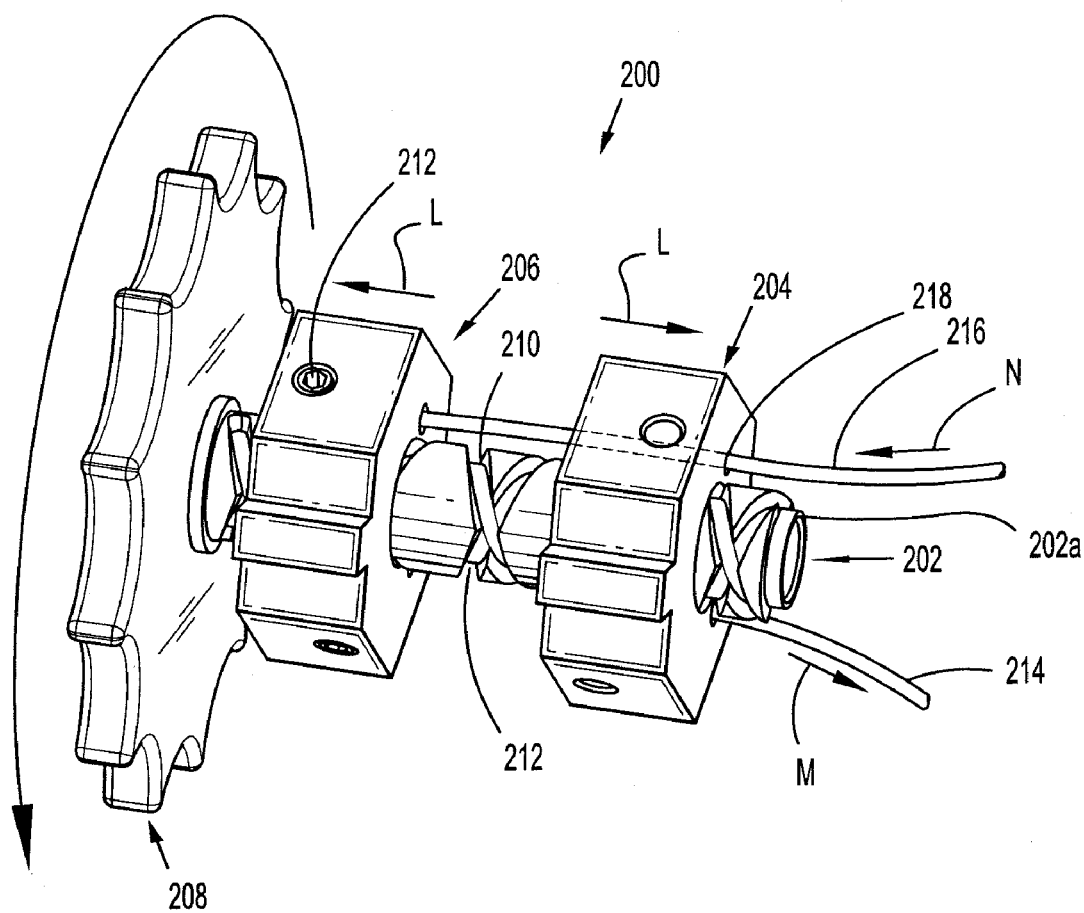
FIG. 30 is a side perspective view of the articulation mechanism of FIG. 28, showing a first rotating member and a second rotating member moving away from each other.
Figure 31:
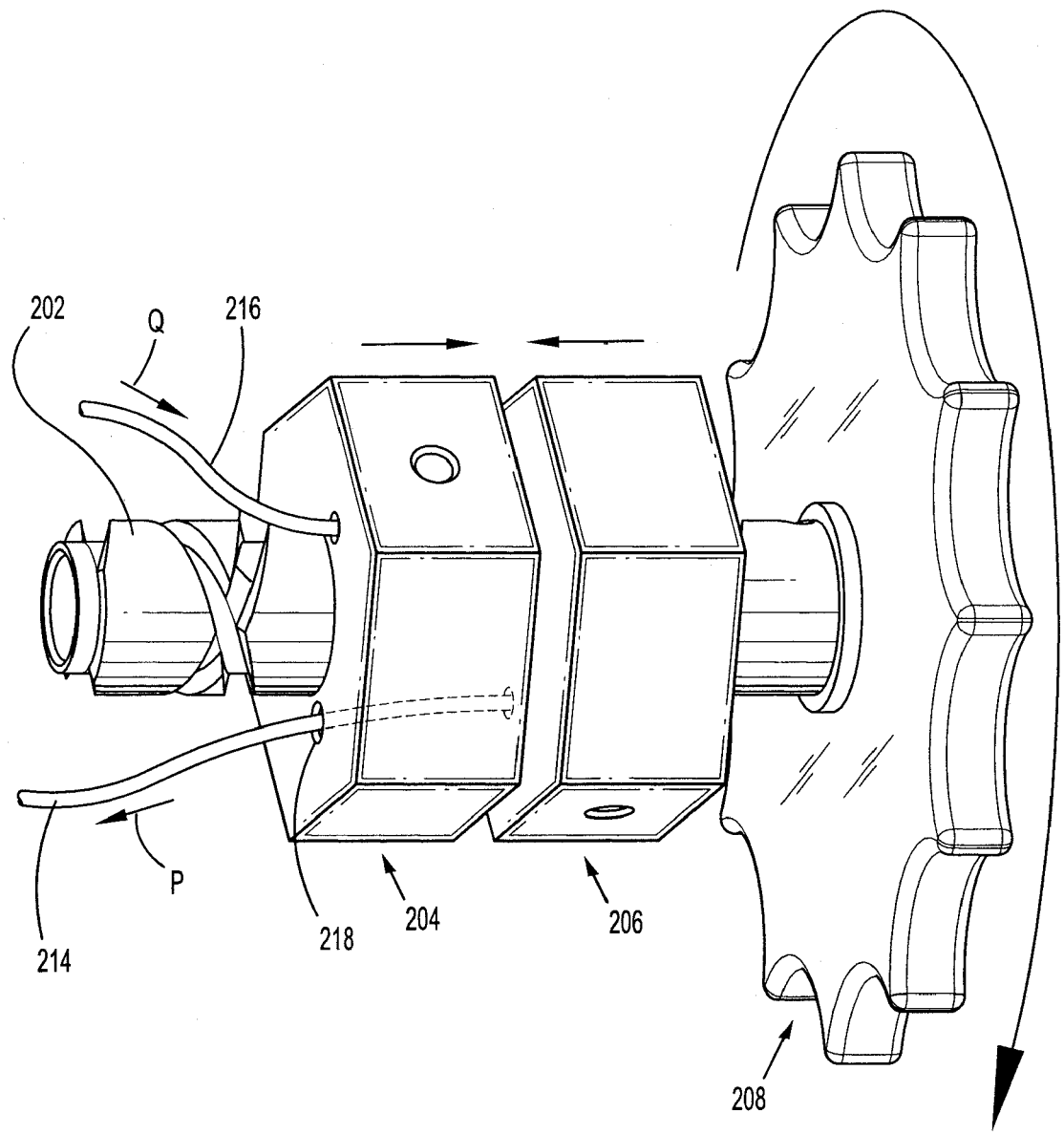
FIG. 31 is a side perspective view of the articulation mechanism of FIG. 28, showing the first rotating member and the second rotating member moving toward each other.

In order to eject fasteners 125, the user advances flexible shaft 122 in a distal direction, as indicated by arrows "G." (See FIGS. 25 and 26). The distal translation of flexible shaft 122 moves drive shaft 154 distally. When drive shaft 154 advances in a distal direction, it engages first pinion gear 194 and disengages outwardly extending protrusions 155 from engagement portion 169 of wobbler 164. Then, the user rotates flexible shaft 122 clockwise, as indicated by arrow "H." (See FIG. 26). As flexible shaft 122 rotates clockwise, drive shaft 154 and first pinion gear 194 rotate clockwise, as indicated by arrow "I." (See FIG. 28). The rotation of first pinion gear 194 causes the rotation of second and third pinion gears 195, 196 in a counterclockwise direction, as indicated by arrows "J." (See FIG. 27). While second and third pinion gears 195, 196 rotate, first and second long lead screws 139, 137 rotate, thereby advancing actuation sled 135 distally through cartridge 107, as indicated by arrow "K." (See FIG. 25). While moving distally, actuation sled 135 sequentially contacts pushers 131. Pushers 131 then translate vertically within retention slots 105 and eject fasteners 125. Fastener deforming concavities 113 deform the legs of fasteners 125 as the pushers 131 drive fasteners toward anvil 192. Thereafter, the user has the option of moving actuation sled 135 proximally by rotating flexible shaft 122 in a counterclockwise direction.

With reference to FIGS. 28-31, the present disclosure also relates to an articulation mechanism 200 for use with surgical instrument 100 or any other suitable surgical device. Generally, articulation mechanism 200 includes an articulation shaft 202 having first and second ends 202a, 202b, a first rotating member 204, a second rotating member 206, and a knob 208 operatively secured to articulation shaft 202. A first cable 214 is attached to first rotating member 204, and a second cable 216 is secured to second rotating member 206. First and second cables 214, 216 are disposed in mechanical cooperation with a tool assembly or a flexible member such that the combined proximal and distal movements of first and second cables 214, 216 articulate the tool assembly or flexible member. Although the drawings show cables, one skilled in the art will recognize that articulation mechanism 200 may include any apparatus capable of steering a tool assembly or a flexible member. First rotating member 204 includes a clearance hole 218 adapted to slidably receive second cable 216. First and second rotating members 204, 206 are mounted on articulation shaft 202. Articulation shaft 202 includes a right-hand groove 212 and a left-hand groove 210 formed thereon. The grooves 210, 212 have a generally helical configuration. It is further contemplated that the grooves 210, 212 may have a fixed or a variable pitch along articulation shaft 202. Additionally, raised ribs may be substituted for the grooves 210, 212.

First rotating member 204 is adapted to engage left-hand groove 210, whereas second rotating member 206 is adapted to engage right-hand groove 212. Each rotating member 204, 206 includes a respective first and second screws 220, 222 for facilitating engagement with the corresponding grooves 210, 212 of articulation shaft 202. First rotating member 204 has a hole 224 configured to receive first screw 220, and second rotating member 206 has a hole 226 adapted to receive second screw 222. During operation, first screw 220 engages left-hand groove 210, and second screw 222 engages right-hand groove 212. In addition, knob 208 is operatively secured to second end 202b of articulation shaft 202. It is contemplated that other structures may be included for facilitating engagement between articulation shaft 202 and the first and second rotating members 204, 206. For example, a post or recess may be located on an interior surface of at least one of first and second rotating members 204, 206, such that it engages and interacts with the respective groove 210, 212 or rib on articulation shaft 202.

Figure 32:
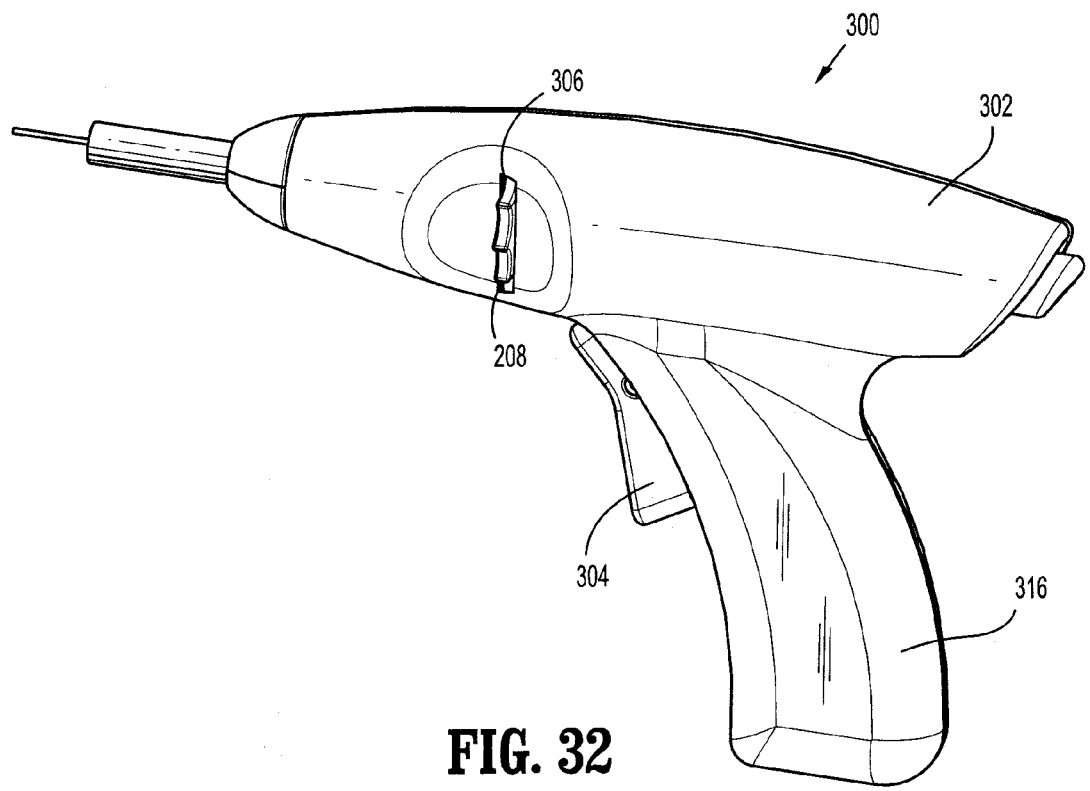
FIG. 32 is a side perspective view of a handle assembly according to an embodiment of the present disclosure.
Figure 33:
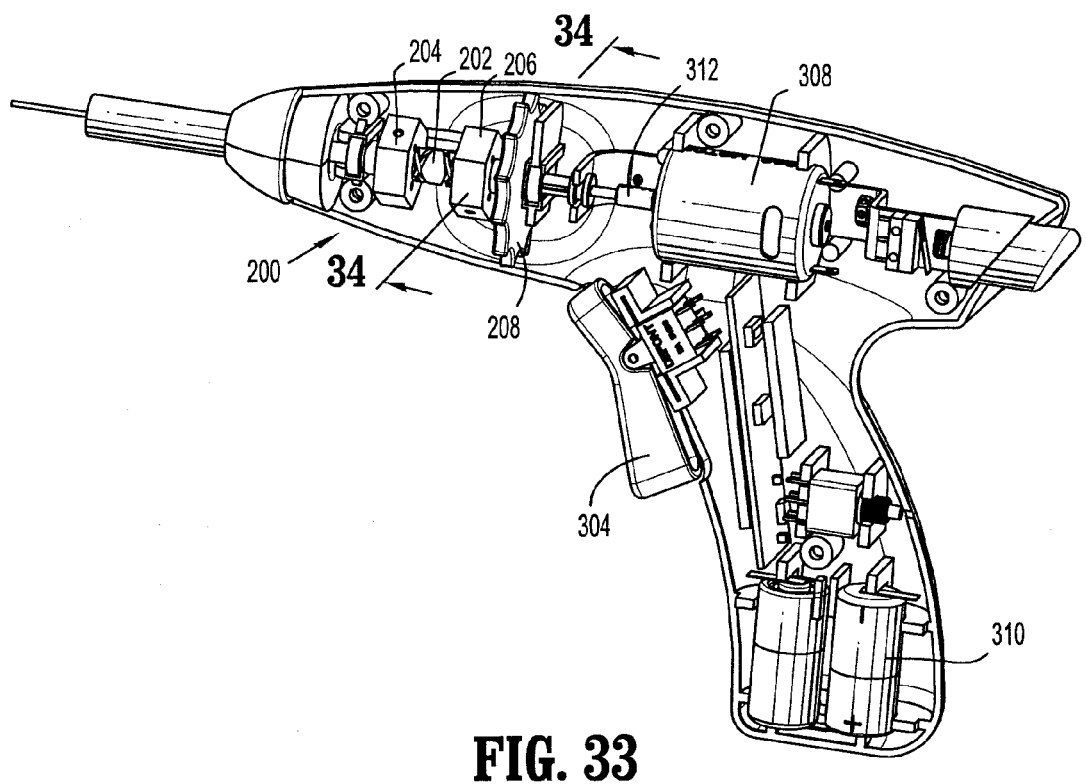
FIG. 33 is a perspective cut away view of the handle assembly of FIG. 32, showing an articulation mechanism, a motor, and a power source.
Figure 34:
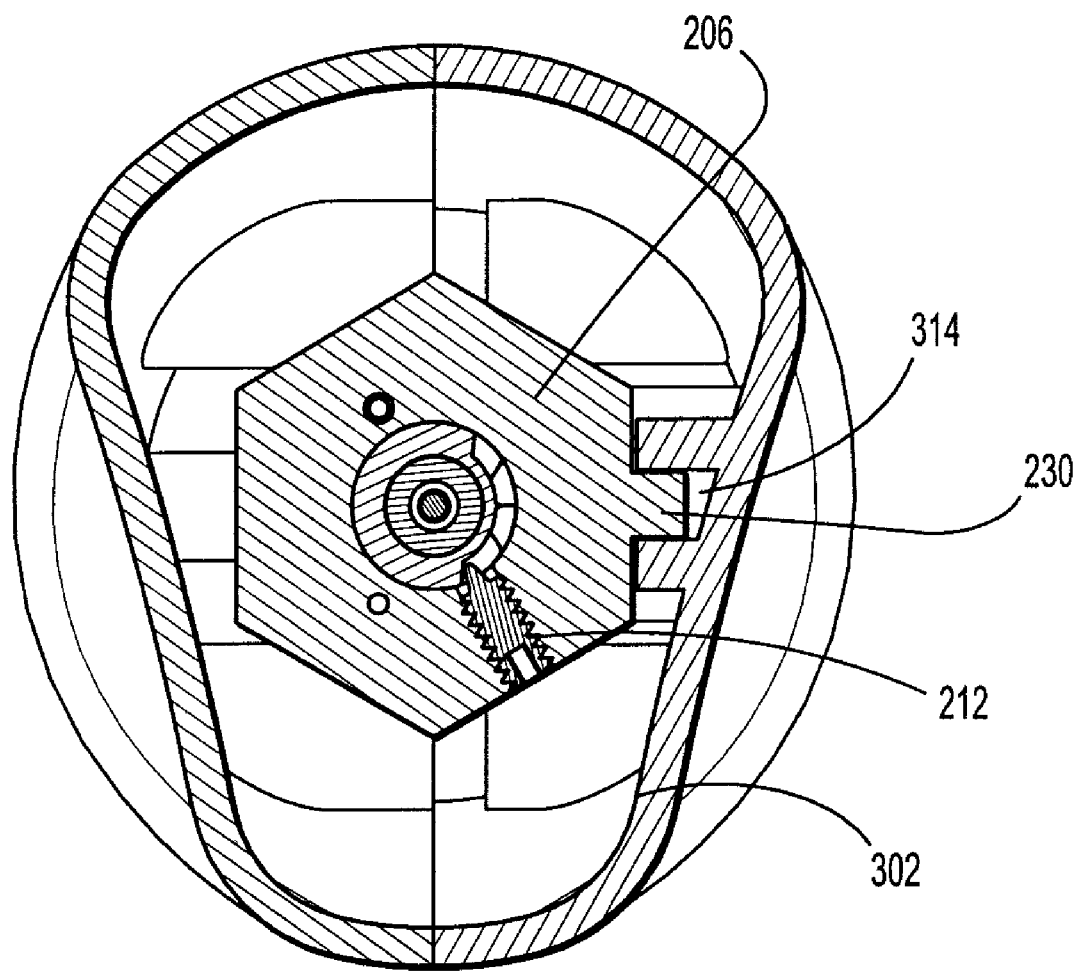
FIG. 34 is a rear cross-sectional view of the handle assembly of FIG. 32 with the articulation mechanism of FIG. 28 disposed therein, taken along section line 34-34 of FIG. 33.

With reference to FIGS. 32-34, in one embodiment, articulation mechanism 200 is operatively associated with a handle assembly 300. Though the drawings show articulation mechanism 200 operatively associated with handle assembly 300, one skilled in the art will recognize that articulation mechanism 200 may be used in conjunction with any suitable actuation apparatus. Handle assembly 300 is configured to rotate articulation shaft 202 and includes a housing 302, a trigger 304 disposed on a handle 316, and an external slit 306 for partially receiving knob 208. Housing 302 encompass a motor 308, a power source 310 for energizing motor 308, and articulation mechanism 200. Power source 310 provides energy to motor 308 upon actuation of trigger 304. Thus, trigger 304 is disposed in electro-mechanical cooperation with motor 308 and power source 310. Motor 308 includes a transmission shaft 312 that extends longitudinally through articulation shaft 202 and is operatively coupled to flexible shaft 122. (See FIG. 19). During operation, when motor 308 is turned on, transmission shaft 312 rotates flexible shaft 122, thereby rotating drive shaft 154.

In operation, a user may alternatively rotate articulation shaft 202 manually through knob 208. When knob 208 is rotated in a clockwise direction, articulation shaft 202 rotates clockwise and moves first and second rotating members 204, 204 longitudinally away from each other, as indicated by arrows "L" in FIG. 28. This longitudinal motion of first and second rotating members 204, 206 translates first cable 214 in the direction indicated by arrow "M" and second cable 216 in the direction indicated by arrow "N." The combined movement of first and second cables 214, 216 articulates a distal portion of any suitable surgical instrument.

On the contrary, when knob 208 rotates in a counterclockwise direction, articulation shaft 202 rotates counterclockwise and approximates first and second rotating members 204, 206 toward each other, as indicated by arrows "0" of FIG. 34. This motion of first and second rotating members 204, 206 advances first cable 214 in the direction indicated by arrow "P" and second cable 216 in the direction indicated by arrow "Q." (See FIG. 31). The combined motion of first and second cables 214, 216 articulates a distal portion of any suitable surgical instrument.

In one embodiment, housing 302 includes a longitudinal slot 314 adapted to receive tabs 228, 230 of first and second rotating members 204, 206, as seen in FIG. 34. Tab 228 protrudes from first rotating member 204, whereas tab 230 protrudes from second rotating member 206. When articulation mechanism 200 is positioned inside housing 302, tabs 228, 230 are located within longitudinal slot 314 and, during operation, prevent first and second rotating members 204, 206 from rotating as articulation shaft 202 rotates.

It will be understood that various modifications may be made to the embodiments disclosed herein. For example, articulation mechanism 200 may be operatively to any suitable medical instrument or tool other than surgical instrument 100. Moreover, other driving mechanism, instead of handle assembly 300, may drive actuation shaft 202 of articulation mechanism 200. Therefore, the above description should not be construed as limiting, but merely as exemplifications of embodiments. Those skilled in the art will envision other modifications within the scope and spirit of the present disclosure.

What is claimed is:

1. A surgical instrument comprising:
a flexible shaft;
a nutating gear drive operatively connected to the flexible shaft, the nutating gear drive configured to reduce a speed and increase a torque of the flexible shaft;
a drive shaft configured to be selectively attached to the nutating gear drive, the drive shaft translatable between an engaged state in which the drive shaft is engaged with the nutating gear drive and a disengaged state in which the drive shaft is disengaged with the nutating gear drive;
a tool assembly including an anvil and a cartridge, the anvil pivotally connected to the cartridge; and
a clamp cam operatively associated with the drive shaft, the clamp cam configured to translate upon rotation of the drive shaft, thereby causing motion of the anvil relative to the cartridge.

2. The surgical instrument according to claim 1, further comprising an actuation sled, the drive shaft adapted to selectively move the actuation sled.

3. The surgical instrument according to claim 2, further comprising a first long lead screw operatively connected to the drive shaft, the first long lead screw being adapted to rotate in response to a rotation of the drive shaft, wherein the actuation sled translates upon rotation of at least the first long lead screw.

4. The surgical instrument according to claim 3, further comprising a first pinion gear operatively connecting the first long lead screw to the drive shaft, wherein the first pinion gear is secured to a distal end of the drive shaft.

5. The surgical instrument according to claim 4, further comprising a second long lead screw operatively connected to the drive shaft, the second long lead screw being adapted to rotate in response to a rotation of the drive shaft, wherein the actuation sled translates upon rotation of the first and second long lead screws.

6. The surgical instrument according to claim 5, further comprising second and third pinion gears configured to rotate upon rotation of the first pinion gear, the second pinion gear attached to a proximal end of the first long lead screw and the third pinion gear attached to a proximal end of the second long lead screw.

7. The surgical instrument according to claim 6, further comprising first and second threaded holes formed in the actuation sled, wherein the first threaded hole is configured to receive the first long lead screw and the second threaded hole is configured to receive the second long lead screw.

8. The surgical instrument according to claim 1, wherein the clamp cam includes a contoured surface slidably receiving a proximal portion of the anvil, the contoured surfaces adapted to direct the motion of the anvil relative to the cartridge.

9. The surgical instrument according to claim 1, wherein the drive shaft includes an outwardly extending protrusion configured to engage the nutating gear drive when the drive shaft is in the engaged state.

10. The surgical instrument according to claim 9, wherein the nutating gear drive includes an engagement portion configured to engage the outwardly extending protrusion when the drive shaft is in the engaged state.

11. The surgical instrument according to claim 10, wherein the engagement portion is a cross-shaped recess.

* * * * *